(12) United States Patent
Ferree

(10) Patent No.: US 8,337,529 B2
(45) Date of Patent: Dec. 25, 2012

(54) METHODS OF BONE, JOINT, AND LIGAMENT RECONSTRUCTION

(75) Inventor: Bret A. Ferree, Cincinnati, OH (US)

(73) Assignee: Anova Corp., Summit, NJ (US)

( * ) Notice: Subject to any disclaimer, the term of this patent is extended or adjusted under 35 U.S.C. 154(b) by 1241 days.

(21) Appl. No.: 12/030,109

(22) Filed: Feb. 12, 2008

(65) Prior Publication Data

US 2008/0195151 A1 Aug. 14, 2008

Related U.S. Application Data

(60) Provisional application No. 60/901,230, filed on Feb. 13, 2007.

(51) Int. Cl.
| | |
|---|---|
| A61B 17/56 | (2006.01) |
| A61B 17/58 | (2006.01) |
| A61B 17/82 | (2006.01) |
| A61B 17/70 | (2006.01) |
| A61B 17/88 | (2006.01) |
| A61F 2/30 | (2006.01) |
| A61F 2/46 | (2006.01) |
| A61F 2/44 | (2006.01) |

(52) U.S. Cl. ......... 606/279; 606/263; 606/86 R; 606/74; 606/76; 623/17.11

(58) Field of Classification Search ............ 606/74, 606/76, 86 R, 263, 279; 623/17.11–17.16
See application file for complete search history.

(56) References Cited

U.S. PATENT DOCUMENTS

| | | |
|---|---|---|
| 3,997,138 A | 12/1976 | Crock et al. |
| 4,146,022 A | 3/1979 | Johnson et al. |
| 4,854,304 A | 8/1989 | Zielke |
| 4,966,600 A | 10/1990 | Songer et al. |
| 5,092,867 A | 3/1992 | Harms et al. |
| 5,108,397 A | 4/1992 | White |
| 5,342,361 A | 8/1994 | Yuan et al. |
| 5,352,224 A | 10/1994 | Westermann |
| 5,387,213 A | 2/1995 | Breard et al. |
| 5,423,820 A | 6/1995 | Miller et al. |
| 5,496,318 A | 3/1996 | Howland et al. |
| 5,611,801 A | 3/1997 | Songer |
| 5,702,399 A | 12/1997 | Kilpela et al. |
| 5,704,936 A | 1/1998 | Mazel |

(Continued)

*Primary Examiner* — Kevin T Truong
*Assistant Examiner* — David Bates
(74) *Attorney, Agent, or Firm* — Pandiscio & Pandiscio

(57) ABSTRACT

Spinal stabilization mechanisms act to prevent lateral bending, extension, and rotation across adjacent vertebrae. Methods for spinal stabilization includes placing one or more anchors at each vertebral level, positioning one or more sutures around each anchor at each level such that the each suture forms a loop or band around two adjacent anchors, applying tension to the ends of each suture to tighten the suture loop around the anchors and welding overlapping ends of each suture together to form suture bands connecting the anchors and thereby preventing lateral bending, extension, and rotation of the spinal segment. An in-growth component is placed over the anterior portions of the three adjacent vertebrae and the disk space therebetween. An anti-adhesion patch is placed over the in-growth component, anchors and elongate members. The anti-adhesion patch has one or more notches that provide access to at least two of the anchors and a flap extending from between the notches. Another elongate member is around the exposed anchors and over a portion of the anti-adhesion patch. Tension is applied to the elongate member to hold the anti-adhesion patch in place. The flap of the anti-adhesion patch is then folded back over the exposed anchors and elongate member.

3 Claims, 20 Drawing Sheets

U.S. PATENT DOCUMENTS

| | | | |
|---|---|---|---|
| 5,725,582 A | 3/1998 | Bevan et al. | |
| 5,782,831 A | 7/1998 | Sherman et al. | |
| 5,904,682 A | 5/1999 | Rogozinski | |
| RE36,221 E | 6/1999 | Breard et al. | |
| 5,964,769 A | 10/1999 | Wagner et al. | |
| 5,989,256 A | 11/1999 | Kuslich et al. | |
| 5,993,448 A | 11/1999 | Remmler | |
| 5,997,542 A | 12/1999 | Burke | |
| 6,033,429 A | 3/2000 | Magovern | |
| 6,093,205 A * | 7/2000 | McLeod et al. | 623/17.16 |
| 6,248,106 B1 | 6/2001 | Ferree | |
| 6,287,308 B1 | 9/2001 | Betz et al. | |
| 6,296,643 B1 | 10/2001 | Hopf et al. | |
| 6,423,065 B2 | 7/2002 | Ferree | |
| 6,626,909 B2 * | 9/2003 | Chin | 606/276 |
| 6,645,211 B2 * | 11/2003 | Magana | 606/247 |
| 6,878,167 B2 * | 4/2005 | Ferree | 623/17.16 |
| 7,090,675 B2 * | 8/2006 | Songer | 606/247 |
| 7,201,774 B2 | 4/2007 | Ferree | |
| 7,776,069 B2 * | 8/2010 | Taylor | 606/249 |
| 8,162,993 B2 * | 4/2012 | Ferree | 606/279 |
| 8,177,810 B2 * | 5/2012 | Ferree | 606/246 |
| 2001/0027319 A1 * | 10/2001 | Ferree | 606/61 |
| 2004/0260287 A1 * | 12/2004 | Ferree | 606/61 |
| 2005/0043733 A1 * | 2/2005 | Eisermann et al. | 606/61 |
| 2006/0009846 A1 * | 1/2006 | Trieu et al. | 623/17.11 |
| 2007/0005062 A1 * | 1/2007 | Lange et al. | 606/61 |
| 2007/0276494 A1 | 11/2007 | Ferree | |
| 2008/0125779 A1 | 5/2008 | Ferree | |
| 2008/0125780 A1 | 5/2008 | Ferree | |
| 2008/0140123 A1 | 6/2008 | Ferree | |
| 2008/0262550 A1 * | 10/2008 | Ferree | 606/263 |
| 2010/0249783 A1 * | 9/2010 | Trieu | 606/76 |
| 2011/0034975 A1 | 2/2011 | Ferree | |

* cited by examiner

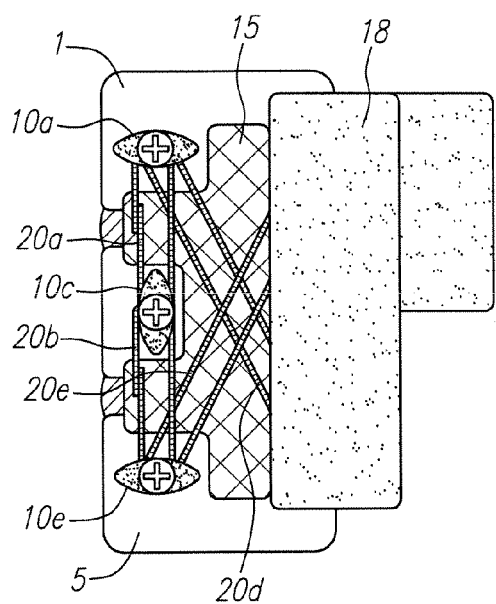
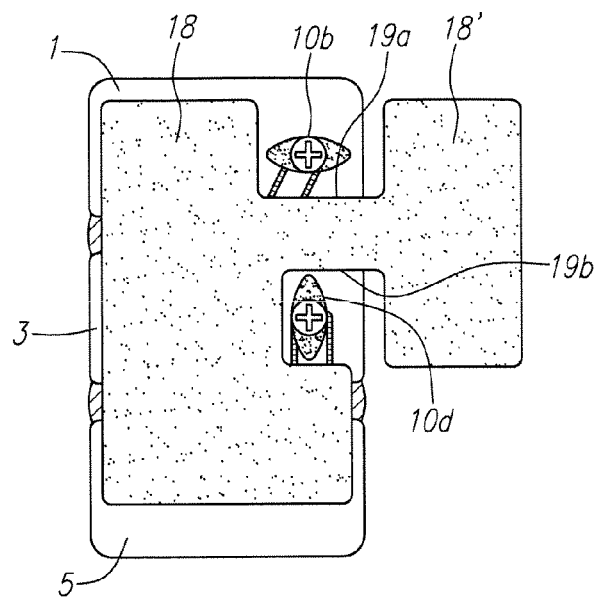
FIG. 1E        FIG. 1F
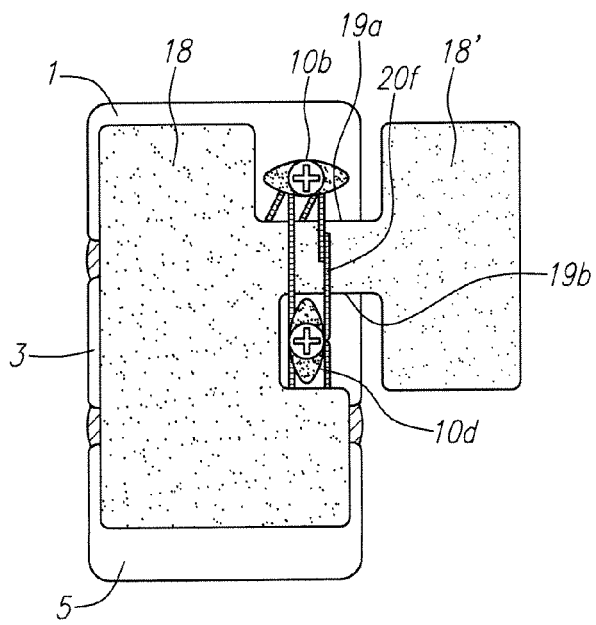
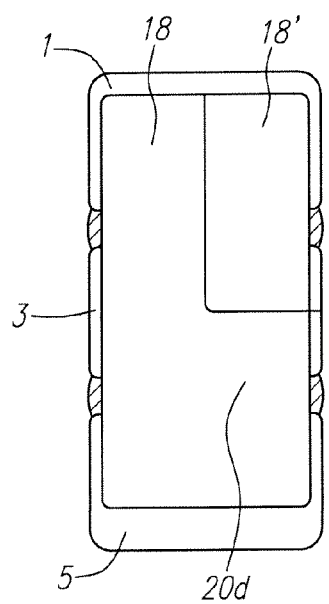
FIG. 1G        FIG. 1H

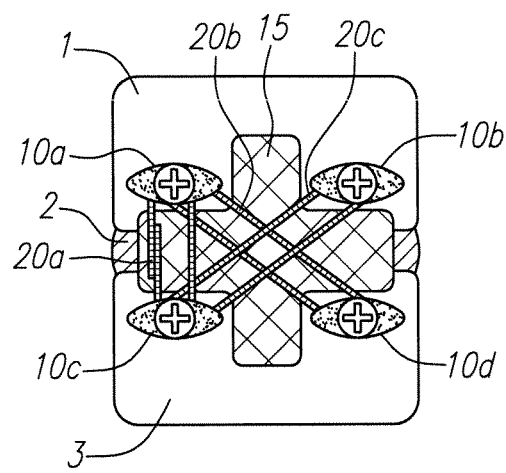
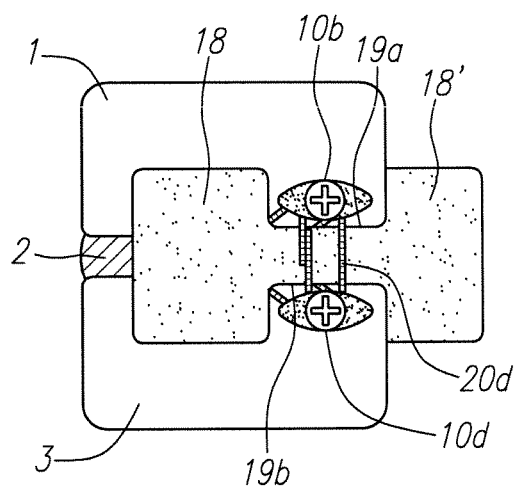
FIG. 2A                FIG. 2B
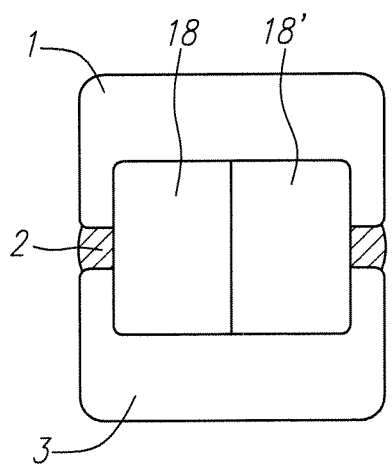
FIG. 2C

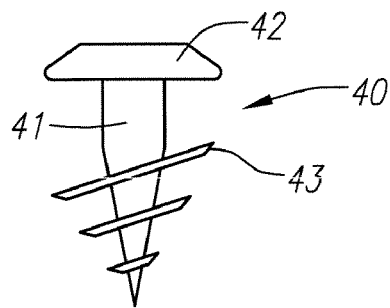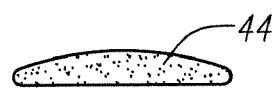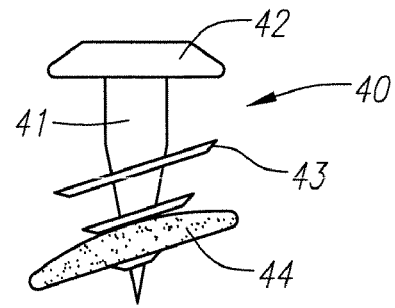
FIG. 12A
FIG. 12B
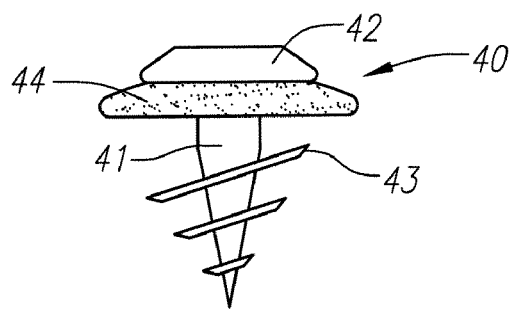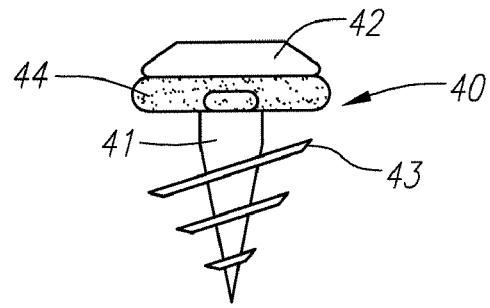
FIG. 12C
FIG. 12D

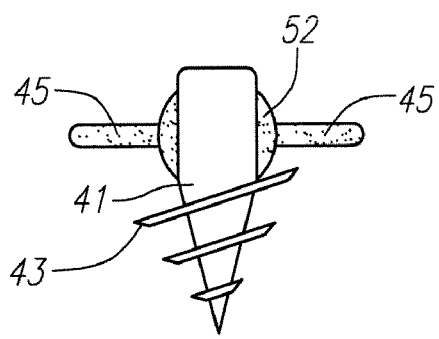
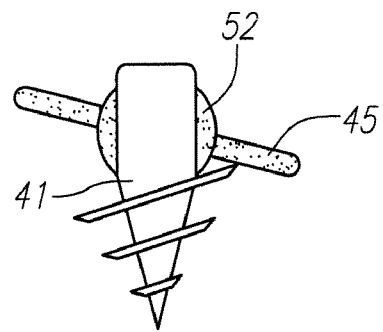
*FIG. 14A*  *FIG. 14B*
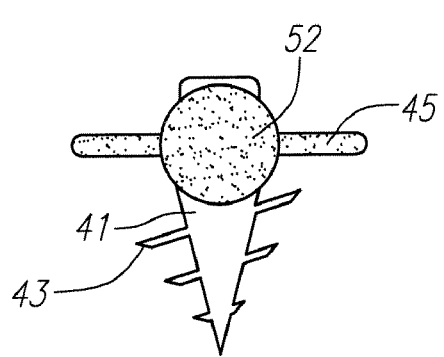
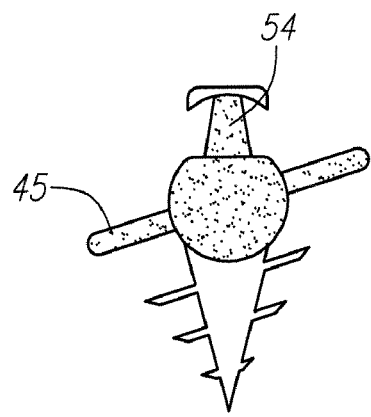
*FIG. 14C*  *FIG. 15*

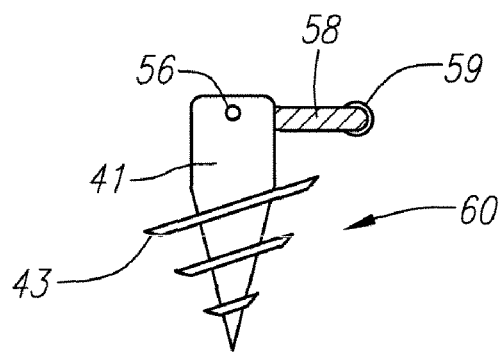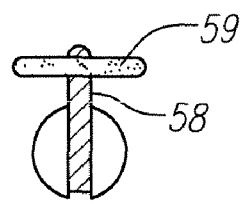
FIG. 16A  FIG. 16B
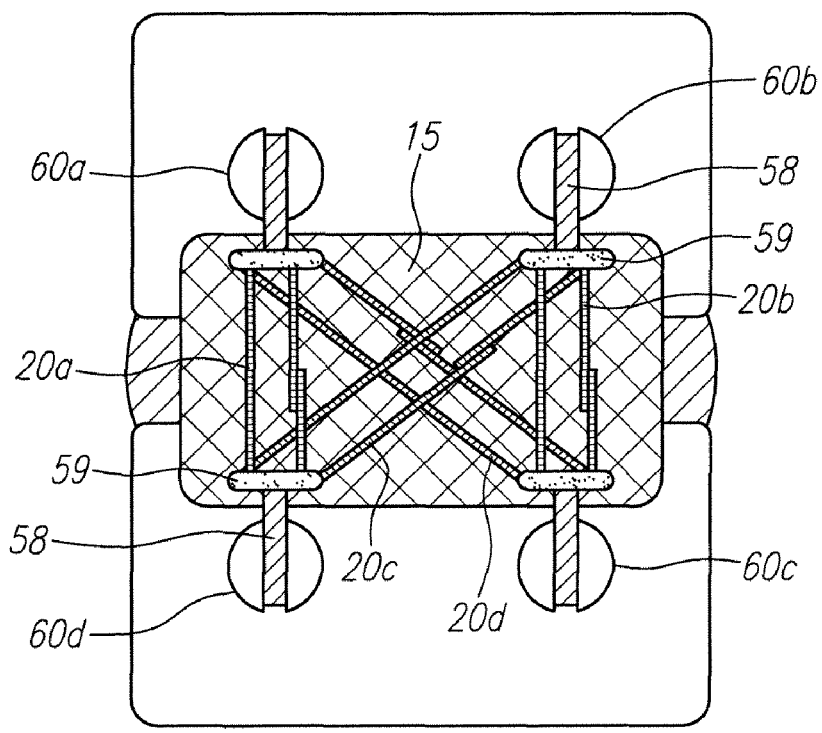
FIG. 17

METHODS OF BONE, JOINT, AND LIGAMENT RECONSTRUCTION

RELATED APPLICATIONS

This application claims the benefit of U.S. Provisional Application No. 60/901,230, filed Feb. 13, 2007, entitled "Bone, Joint and Ligament Reconstruction with Bands." This application is related to applications 60/808,795, filed May 26, 2006, entitled "Fastening Assemblies for Disc Herniation Repair and Methods of Use" and 60/861,499, filed Nov. 28, 2006, entitled "Annulus and Spinal Ligament Reconstruction." The application is also related to U.S. Pat. Nos. 6,248, 106 and 6,423,065. All of the above-referenced patent and applications are hereby expressly incorporated by reference in their entirety.

FIELD OF THE INVENTION

The subject invention resides in methods and apparatus for bone, joint and ligament reconstruction including reconstructing the annulus fibrosis (AF) of a spinal disc and the ligaments of the spine. The invention is particularly well suited to the prevention of extrusion of material or devices placed into the disc space and to the prevention of excessive spinal motion.

BACKGROUND

The human intervertebral disc is an oval to kidney bean-shaped structure of variable size depending on the location in the spine. The outer portion of the disc is known as the annulus fibrosis (AF). The annulus fibrosis is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The annulus fibrosis contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. This disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the annulus fibrosis. As discussed in co-pending U.S. patent application Ser. No. 10/407,554 and U.S. Pat. No. 6,878,167, the content of each being expressly incorporated herein by reference in their entirety, the posterior portion of the annulus fibrosis has abundant pain fibers.

Herniated nucleus pulposus (HNP) occurs from tears in the annulus fibrosis. The herniated nucleus pulposus often allies pressure on the nerves or spinal cord. Compressed nerves cause back and leg or arm pain. Although a patient's symptoms result primarily from pressure by the nucleus pulposus, the primary pathology lies in the annulus fibrosis.

Surgery for herniated nucleus pulposus, known as microlumbar discectomy (MLD), only addresses the nucleus pulposus. The opening in the annulus fibrosis is enlarged during surgery, further weakening the annulus fibrosis. Surgeons also remove generous amounts of the nucleus pulposus to reduce the risk of extruding additional pieces of nucleus pulposus through the defect in the annulus fibrosis. Although microlumbar discectomy decreases or eliminates a patient's leg or arm pain, the procedure damages weakened discs.

SUMMARY

A portion of the annulus fibrosis and a portion of the ligaments of the spine are excised to allow insertion of materials and devices into the disc space. For example, a portion of the anterior half of the annulus fibrosis and a portion of the anterior longitudinal ligament (ALL) are excised to enable insertion of bone growth promoting materials and fusion devices in interbody fusion procedures. Removal of portions of the annulus fibrosis and anterior longitudinal ligament increase the flexibility of the spine and allow excessive motion of the spine. For example, removal of the tissues mentioned permits excessive spinal extension, lateral bending, and axial rotation. Destabilizing the spine decreases the chance of a successful fusion. The invention may be used to increase the stiffness of the operated segment of the spine. Increasing the stiffness of the spine facilitates spinal fusion.

A portion of the annulus fibrosis and a portion of the anterior longitudinal ligament are also excised to enable insertion of motion preserving devices into the disc. For example, Total Disc Replacements (TDRs) and Nucleus Replacements (NRs) are often inserted through the anterior portion of discs. Excessive spinal extension, lateral bending, and axial rotation following excision of the spinal tissues and insertion of motion preserving devices into the disc space places excessive force on the facets of the spine. Biomechanical studies show the forces across the facets at the operated level of the spine can be doubled by motion preserving devices and the techniques used to insert such devices. Excessive force on the facets may lead to degeneration of the facets. Degeneration of the facets may cause low back pain.

The present invention provides methods for spinal stabilization operative to prevent lateral bending, extension, and rotation across adjacent vertebrae. Broadly, the method includes placing two or more anchors at each vertebral level, placing an in-growth component over the anterior portion of the adjacent vertebra and the space therebetween, passing one or more sutures through each anchor at each level, applying tension to the sutures and joining the sutures in a cross-braced arrangement over the in-growth component to hold the in growth component against the spine and to prevent lateral bending, extension, and rotation of the spinal segment.

In some embodiments, four anchors can be used to join two adjacent vertebrae. Two anchors each having at least one elongate member, such as a suture, extending therethrough are placed in each vertebra. An in-growth component is placed over the anterior portions of the vertebrae and the disk space therebetween. In some embodiments, the in growth component can have lateral extensions that lie between the anchors. The elongate members are attached in a crossing pattern over the in-growth component and tension is applied to the elongate members to press the in-growth component into the spine and to prevent lateral bending, extension, and rotation across the adjacent vertebrae. An anti-adhesion patch is placed over the in-growth component, anchors and elongate members. The anti-adhesion patch has one or more notches that provide access to one or more of the anchors and a flap extending from between the notches. Another elongate member is placed around the exposed anchors and over a portion of the anti-adhesion patch. Tension is applied to the elongate member to hold the anti-adhesion patch in place. The flap of the anti-adhesion patch is then folded back over the exposed anchors and elongate member. In some embodiments, the sutures can be made of different material and have different properties.

In some embodiments, the elongate members can comprise sutures which can be joined by welding. In other embodiments, the elongate members can comprise pre-formed suture bands. In some embodiments, the in growth component can comprise a mesh patch selected such that connective tissue will grow into and over the mesh in vivo, forming a synthetic tendon-like layer that further cushions and protects spinal segment.

In an alternative embodiment, multiple anchors and sutures can be used to provide additional stabilization/fixation across three adjacent vertebrae. An in-growth component is placed over the anterior portions of the three adjacent vertebrae and the disk space therebetween. The in growth component can have lateral extensions that extend between the anchors. The elongate members can be attached in any combination of vertical and diagonal patterns over the in-growth component and joined together to press the in-growth component against the spine. Tension can be applied to the sutures prior to joining them together to vary the resistance to spinal extension, lateral bending and axial rotation extension as necessary. An anti-adhesion patch is placed over the in-growth component, anchors and elongate members. The anti-adhesion patch has one or more notches that provide access to at least two of the anchors and a flap extending from between the notches. Another elongate member is around the exposed anchors and over a portion of the anti-adhesion patch. Tension is applied to the elongate member to hold the anti-adhesion patch in place. The flap of the anti-adhesion patch is then folded back over the exposed anchors and elongate member.

In an alternative embodiment, multiple anchors and sutures can be used to provide stabilization/fixation across a lumbar vertebra and the sacrum. Two anchors each having at least one elongate member, such as a suture, extending there through are placed in the lumbar vertebra and two anchors are placed in the sacrum. An in-growth component is placed over the anterior portions of the lumbar vertebra and the sacrum located between the anchors as well the disk space there between. In some embodiments, the in growth component can have lateral extensions that extend beyond the anchors. The elongate members can be attached in any combination of vertical and diagonal patterns between the anchors in the lumbar vertebra and the sacrum. The elongate members are placed over the in-growth component and joined together to press the in-growth component into the spine. Tension can be applied to the elongate members prior to joining them together to vary the resistance to spinal extension, lateral bending and axial rotation extension as necessary. In some embodiments, a third anchor can be placed in the lumbar vertebra and in the sacrum to provide additional stabilization/fixation across two adjacent vertebrae. An anti-adhesion patch is placed over the in-growth component, anchors and elongate members. The anti-adhesion patch has one or more notches that provide access to at least two of the anchors and a flap extending from between the notches. Another elongate member is placed around the exposed anchors and over a portion of the anti-adhesion patch. Tension is applied to the elongate member to hold the anti-adhesion patch in place. The flap of the anti-adhesion patch is then folded back over the exposed anchors and elongate member.

The invention may incorporate materials that encourage the growth of connective tissue into components of the various devices taught in the invention. The invention may also incorporate materials that prevent the growth of connective tissue into components of the various devices taught in the invention. Preventing or limiting connective in-growth may be used to diminish adhesions at the surgical site.

The invention may also be used to treat other orthopedic conditions. For example, the invention may be used to treat fractures, such as fractures of the patella and olecranon. The invention may also be used to immobilize joints during fusion procedures. The invention may also be used with prosthetic joints.

BRIEF DESCRIPTION OF THE DRAWINGS

FIG. 1E is an anterior view of the embodiment in FIG. 1D illustrating the anti-adhesion component partially covering the in-growth component, anchors and elongate members.

FIG. 1F is an anterior view of the embodiment in FIG. 1E illustrating anti-adhesion component with openings exposing at least two of the anchors.

FIG. 1G is an anterior view of the embodiment in FIG. 1F illustrating another elongate member placed over the anti-adhesion cover and connecting the exposed anchors.

FIG. 1H is an anterior view of the embodiment in FIG. 1G illustrating the flap of the anti-adhesion component folded back over the exposed anchors and elongate member.

FIG. 2A is an anterior view of an alternative embodiment for stabilizing two adjacent vertebrae.

FIG. 2B is an anterior view of the embodiment in FIG. 2A illustrating the anti-adhesion component with notches exposing at least two anchors and an elongate member placed over the anti-adhesion cover and connecting the exposed anchors.

FIG. 2C is an anterior view of the embodiment in FIG. 2B illustrating the anti-adhesion component folded back over the exposed anchors and elongate member.

FIG. 12A is an exploded lateral view of an anchor suitable for use in the above described embodiments.

FIG. 12B is a lateral view of the embodiment of the invention drawn in FIG. 12A.

FIG. 12C is a lateral view of the embodiment of the invention drawn in FIG. 12B.

FIG. 12D is an anterior view of the embodiment of the invention drawn in FIG. 12C.

FIG. 14A is a lateral view of an alternative anchor suitable for use in the above described embodiments.

FIG. 14B is a lateral view of the embodiment of the invention drawn in FIG. 14A.

FIG. 14C is a sagittal cross section through the embodiment of the invention drawn in FIG. 14A.

FIG. 15 is a sagittal cross-section through an alternative anchor suitable for use with the above described embodiments.

FIG. 16A is a lateral view of an alternative anchor suitable for use with the above described embodiments.

FIG. 16B is view of the top of the embodiment of the invention drawn in FIG. 16A.

FIG. 17 is an anterior view of a portion of the spine and the embodiments of the invention drawn in FIGS. 2A and 16.

DETAILED DESCRIPTION

Devices in Various Spinal Segments

Figure 1A:
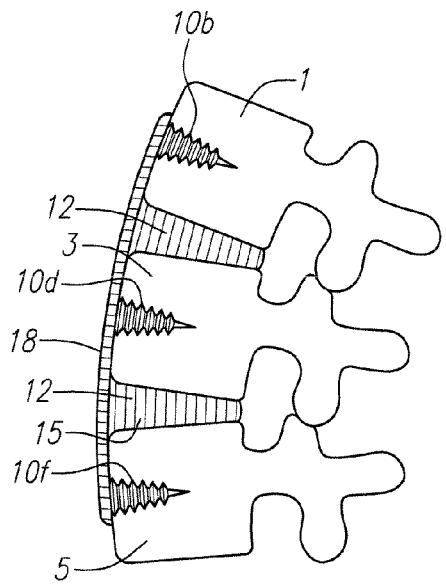
FIG. 1A is a lateral view of a sagittal cross section of an embodiment for stabilizing three adjacent vertebrae.

FIG. 1A is a lateral view of a sagittal cross section of a portion of the spine. Anchors 10b, d, and f were placed into the anterior portions of vertebrae 1, 3, and 5, respectively. Intradiscal devices 12, such as spinal cages filled with bone growth promoting material, were placed into the disc space. The intradiscal devices are preferably trapezoidal in shape. The trapezoidal cages help preserve the natural lordosis of the spine, which is the normal inward curvature of the lower region of the spine resulting in a concave back as viewed from the side. The intradiscal devices are preferably sized to fill the entire disc space. Flexible longitudinal fixation elements, such as elongate bands or welded sutures, connect anchors 10b, d, and f. In-growth component 15, preferably made of polyester mesh, lies between an anti-adhesion component 18 or cover, such as an ePTFE component, and the anterior portion of the spine.

Figure 1B:
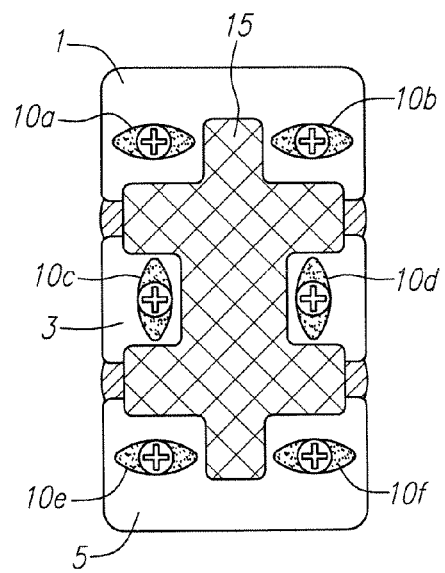
FIG. 1B is an anterior view of the embodiment in FIG. 1A for joining three adjacent vertebrae.

FIG. 1B is an anterior view of a portion of the spine and the embodiment of the invention drawn in FIG. 1A. Anchors 10a-f were placed into three adjacent vertebrae 1, 3, and 5. Alternatively, the anchors could be limited to vertebrae 1, 5 at the ends of the construct (spinal segment). The anchors 10a-f can vary in size from about 3 to about 12 mm in diameter and about 4 to about 40 mm in length. For example, anchors having a diameter of about 3 mm and a length of about 7 mm can be used in the anterior portions of cervical vertebrae. Additionally, anchors having a diameter of about 8 mm and a length of about 35 mm can be used in the anterior portions of lumber vertebrae. The anchors are preferably made of an MRI-compatible material. For example, the anchors can be made of titanium, plastic, or other material. The anchors can additionally be coated with a material, such as hydroxyappetite, that promotes the in-growth of bone. In an alternative embodiment, the anchors can be hollow and filled with a material that promotes bone in-growth. In some embodiments, the anchors can have one or more eyelets for threading one or more sutures therethrough. In alternative embodiments, the anchors can have an enlarged head or a separate transverse elongate member at the head of the anchor for wrapping a suture band around the anchor. Examples of anchors suitable for use with the following methods are described in further detail in U.S. Pat. No. 6,248,106, entitled "Cross-Coupled Vertebral Stabilizers," issued on Jun. 19, 2001, U.S. Pat. No. 6,423,065, entitled "Cross-Coupled Vertebral Stabilizers Including CAM-operated Cable Connectors," issued on Jul. 23, 2002, U.S. patent application Ser. No. 11/805,677, "entitled "Fastening Assemblies for Disc Herniation Repair and Methods of Use," filed on May 23, 2007, U.S. patent application Ser. No. 11/945,994, "entitled "Methods of Anterior Fixation and Stabilization of a Spinal Segment," filed on Nov. 27, 2007, all of which are incorporated in their entirety herein An in-growth component 15 lies over the anterior portion of the vertebrae 1, 3 and 5 and the disc space therebetween. The in-growth component preferably has lateral extensions that extend between anchors 10b and 10d, 10d and 10f, 10e and 10c, and 10a and 10c. The anchors do not pass through the in-growth component. In some embodiments, the in-growth component can comprise a mesh patch. The mesh patch may be made of synthetic materials such as polyester, polypropylene, ePTFE, or polyethylene. Alternatively, the mesh could be made of natural material such as autograft, allograft, or xenograft tissues such as acellular dermis, swine intestinal submucosa, ligaments, facia, or tendon. The mesh patch is preferably about 0.25 mm thick. Alternatively, mesh patch may be about 0.1 to about 2.0 mm thick. The mesh preferably has 1 by 1 mm pores. Alternatively, the mesh may have pores about 0.001 by about 0.005 mm in size to about 1 by about 3 mm in size. The holes in the mesh may be circular or elongate in shape. The mesh preferably has a burst-strength of 50 to 100 PSI. Alternatively, the mesh may have a burst-strength of 25 to 175 PSI. The mesh component is preferably supplied in various sizes to fit in between the adjacent anchors. For example, the mesh may be supplied in a rectangular or square patch in a 10 by 10 mm, 12 by 14 mm, 13 by 20 mm, 14 by 18 mm, and 16 by 50 mm sizes. The mesh patch can have one or more notches cut out to accommodate the anchors. Alternatively, the mesh may be cut by surgeons to properly fit patient's anatomy. The mesh should extend over both sides of the anterior longitudinal ligament 13 and the annulus fibrosis 11 on either side of the annular window. The mesh acts as scaffolding for connective tissue in-growth from the annulus fibrosis 11, the anterior longitudinal ligament 13, and the vertebrae 1, 3, 5. The connective tissue, the in growth component 15, and the fixation sutures 10a-f at least partially reproduce the function of the annulus fibrosis 11 and the anterior longitudinal ligament 13. The components also prevent extrusion of tissue that resides within the disc, such as the nucleus pulposus, or materials or devices that are placed within the disc, such as intradiscal devices 12.

Figure 1C:
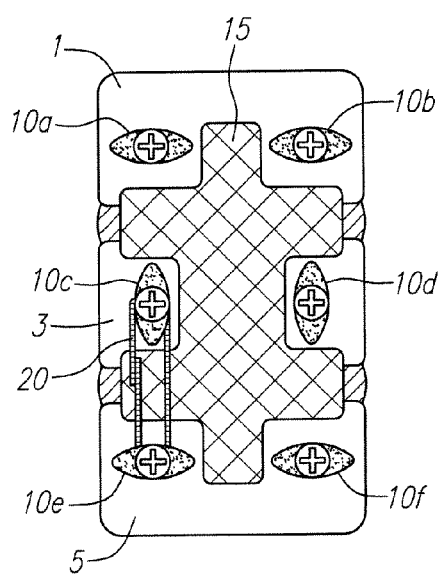
FIG. 1C is an anterior view of the embodiment in FIG. 1B illustrating an elongate band connecting two anchors in adjacent vertebrae.

FIG. 1C is an anterior view of a portion of the spine and the embodiment of the invention drawn in FIG. 1B with an elongate band connecting anchors 10c and 10e. Longitudinal fixation component 20, such as an elongate band or suture, connects anchors 10c, e in the right side of the caudal and intermediate vertebrae 3, 5. The suture 20 is placed over the in-growth component 15 such that tension applied to the suture will press the in-growth component 15 against the spine preventing the in-growth component from migrating and promoting tissue in-growth.

Figure 1D:
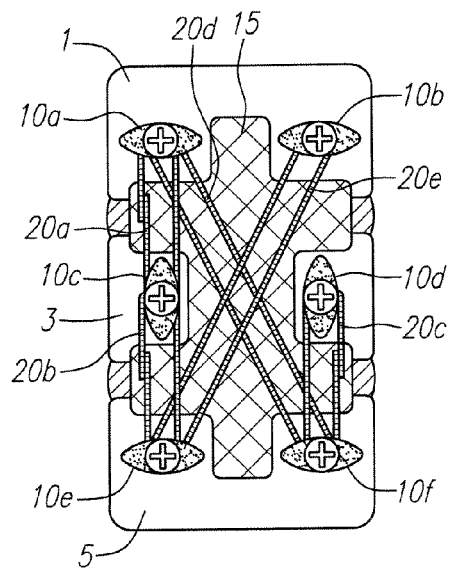
FIG. 1D is an anterior view of the embodiment in FIG. 1C illustrating additional elongate bands connecting anchors in the three adjacent vertebrae.

As shown in FIG. 1D, additional longitudinal fixation components, or sutures, 20a, 20b, 20c, 20d are placed over the in-growth component 15 and around anchors 10a-f to hold the in growth component against the spine and to apply additional tension across the vertebrae 1, 3, 5 in order to prevent lateral bending, extension, and rotation of the spinal segment. The sutures 20a-d can be arranged in any combination of vertical and diagonal patterns between anchors 10a-f to hold the in-growth component against the spine and to apply tension across vertebrae 1, 3, and 5. For example, as illustrated in FIG. 1D, in one embodiment, a first elongate element or band 20b connects anchors 10c, e in the right side of the caudal and intermediate vertebrae 3, 5. A second elongate element or band 20c connects anchors 10d, f in the left side of the caudal and intermediate vertebrae 3, 5. A third elongate element or band connects anchors 10a, c in the right side of the cranial and intermediate vertebrae 1, 3. A fourth elongate element or band 20a connects anchor 10e in the right side of caudal vertebra 5 to anchor 10b in the left side of cranial vertebra 1. A fifth elongate element or band 20e connects the anchor 10f in the left side of caudal vertebra 5 to anchor 10a in the right side of cranial vertebra 1. In general, the anchors may be partially inserted and then fully advanced after the suture bands are looped over the anchors.

The method is advantageous in that it is much quicker and easier than prior methods which required the surgeon to thread one or more sutures through small openings in the in growth component 15 to hold it in place. Moreover, this method eliminates the risk of the sutures cutting through and out of the in-growth component due to tension on the in growth component and allowing the anti-adhesion component to migrate away from the spine.

As illustrated in FIG. 1E, an anti-adhesion component can be placed over the in-growth component 15, anchors 10a-f and vertebrae 1, 3 and 5. Anti-adhesion component 18 is shown lifted from the anchors, elongate elements or bands, and in-growth component 15 and folded to the right hand side of the drawing. The elongate elements or bands 20a-e connect the anchors 10a-f to inhibit or limit motion between the three vertebrae 1, 3, and 5. In-growth component 15 lies between the elongate elements or bands 20a-e and the anterior surface of the vertebrae. The elongate elements or bands 20a-e hold and preferably compress the in-growth component against the spine. The elongate elements or bands 20a-e do not pass through the in-growth 15 or anti-adhesion components 18.

The anti-adhesion cover 18 is made of a material that discourages tissue in-growth or adhesions. For example, anti-adhesion cover 18 may be made of ePTFE, Sepratfilm, allograft, or absorbable materials. These absorbable materials include oxidized atelocollagen type I, polyethylene glycol, glycerol, or combinations thereof. Anti-adhesion cover 18 will have interstitial pore sizes of 3 microns or less to discourage tissue in-growth. Anti-adhesion cover 18 will have a larger size than in-growth component 15 such that anti-adhesion cover 18 completely covers in-growth component 15. Anti-adhesion cover 18 may have a symmetrical or asymmetrical shape. Shapes of anti-adhesion cover 18 may include, but not be limited to, a rectangle, a square, a polygon, a circle, an ellipse, an oval, a planar disc, and a triangle. This will enable complete coverage of in growth component 15, welded sutures 20a-d and anchors 10a0f once it is deployed, thereby discouraging tissue in-growth and adhesions from outside the wound site.

As shown in FIG. 1F, anti-adhesion component 18 comprises a rectangular patch with a width and length sufficient to extend beyond the in-growth component 15, elongate elements or bands 20a-d and anchors 10a-f. At least two notches or openings 19a,b have been made in the anti-adhesion patch 18 to expose at least two anchors 10b, d to enable placement of an elongate element or band therebetween. A flap 18' sized to completely cover the openings 19a,b extends from between the openings 19a,b.

In use, as shown in FIG. 1G, anti-adhesion component 18 is placed over the elongate elements or bands 20a-d, in-growth component 15, and anchors 10a-f such that anchors 10b, d remain exposed via notches 19a,b. An additional elongate element or band 20f, such as a suture band, is placed around the post of anchor 10b in the left side of the cranial vertebra 1 and the post of anchor 10d in the left side of the intermediate vertebra 3. The ends of the elongate element or band 20f are fastened, preferably by ultrasonic welding, in the tightened configuration. The elongate element or band 20f is cut just distal to the fastened or welded area to remove the ends of the elongate element or band distal to the fastened or welded area. Tension is applied to the ends of the elongate element or band 20f after the elongate element is looped around the posts of the anchors 10b, d. Applying tension to the elongate element 20f presses the anti-adhesion cover 18 in place against the spine and prevents migration of the anti-adhesion cover 18. The longitudinal fixation component also further inhibits or limits motion between the cranial and intermediate vertebrae. The method is advantageous in that it is much quicker and easier than prior methods which required threading one or more sutures through small openings in the anti-adhesion cover 18 to hold it in place. Moreover, this method eliminates the risk of the sutures cutting through the anti-adhesion component due to tension on the anti-adhesion component and allowing the anti-adhesion component to migrate away from the spine. Folding over flap 18' results in complete coverage of the in growth component 15, elongate elements 20a-f and anchors 10a-f, as seen in FIG. 1H thereby preventing adhesions to the elongate elements or bands, in-growth component, and the anchors and preventing injury to delicate structures such as nerves, blood vessels, and the esophagus that lie directly over the anchors.

FIG. 1H is an anterior view of a portion of the spine and the preferred embodiment of the invention. Anti-adhesion component 18, preferably ePTFE, has been fastened to the anterior portion of the spine. Flap 18' of anti-adhesion component 18 has been folded over to cover the previously exposed anchors and elongate elements.

FIG. 2A is an anterior view of a portion of the spine and an alternative embodiment of the invention that is used to stabilize a spinal segment comprising two vertebrae and a disc (or disc space) located therebetween. The device connects two vertebrae 1 and 3 and includes an in-growth component 15, set of anchors 10a-d, sets of elongate elements 20a-c, and an anti-adhesion component or cover 18. In-growth component 15 lies over the anterior portion of the spine. In some embodiments, the in-growth component 15 can comprise a mesh patch. The mesh patch may be made of synthetic materials such as polyester, polypropylene, ePTFE, or polyethylene. Alternatively, the mesh could be made of natural material such as autograft, allograft, or xenograft tissues such as acellular dermis, swine intestinal submucosa, ligaments, facia, or tendon. The mesh patch is preferably about 0.25 mm thick. Alternatively, mesh patch may be about 0.1 to about 2.0 mm thick. The mesh preferably has 1 by 1 mm pores. Alternatively, the mesh may have pores about 0.001 by about 0.005 mm in size to about 1 by about 3 mm in size. The mesh patch can have one or more notches cut out to accommodate the anchors. Alternatively, the mesh may be cut by surgeons to properly fit patient's anatomy. The mesh should extend over both sides of the anterior longitudinal ligament 13 and the annulus fibrosis 11 on either side of the annular window. The mesh acts as scaffolding for connective tissue in-growth from the annulus fibrosis 11, the anterior longitudinal ligament 13, and the vertebrae 1 and 3.

Anchors 10a-d were placed into the anterior portions of vertebrae 1, 3. A first elongate element or band 20a connects anchors 10a, c in the right sides of vertebrae 1, 3. A second elongate element or band 20b connects anchor 10d in the left side of caudal vertebra 3 to anchor 10a in the right side of cranial vertebra 1. A third elongate element or band 20c connects anchor 10c in the right side of caudal vertebra 3 to anchor 10b in the left side of cranial vertebra 1. In-growth component 15 lies between the elongate elements or bands 20 and the anterior surface of the spine. The elongate elements 20a-c are placed over the in growth component 15 such that tension applied to the elongate elements 20a-c will press the in-growth component against the spine preventing the in-growth component from migrating and promoting tissue in-growth. The connective tissue, the in growth component 15, and the elongate members 20a-c at least partially reproduce the function of the annulus fibrosis 11 and the anterior longitudinal ligament 13. The components also prevent extrusion of tissue that resides within the disc, such as the nucleus pulposus, or materials or devices that are placed within the disc, such as intradiscal devices 12.

FIG. 2B is an anterior view of a portion of the spine and the embodiment of the invention drawn in FIG. 2A with an anti-adhesion component 18. The anti-adhesion component 18 comprises a rectangular patch with a width and length sufficient to extend beyond the in-growth component 15, elongate elements or bands 20a-c and anchors 10a-d. At least two notches or openings 19a,b have been made in the anti-adhesion patch 18 to expose at least two anchors 10b, d to enable placement of an elongate element or band therebetween. A flap 18' sized to completely cover the openings 19a,b extends from between the openings 19a,b. As discussed above, the anti-adhesion cover 18 is made of a material that discourages tissue in-growth or adhesions. For example, anti-adhesion cover 18 may be made of ePTFE, Sepratfilm, allograft, or absorbable materials. These absorbable materials include oxidized atelocollagen type I, polyethylene glycol, glycerol, or combinations thereof. In addition, anti-adhesion cover 18 will preferably have interstitial pore sizes of 3 microns or less to discourage tissue in-growth.

In use, as shown in FIG. 2B, an additional elongate element or band 20d, such as a suture band, is placed around the post of anchor 10b in the left side of the cranial vertebra 1 and the post of anchor 10d in the left side of caudal vertebra 3. The ends of the elongate element or band 20d are fastened, preferably by ultrasonic welding, in the tightened configuration. The elongate element or band 20d is cut just distal to the fastened or welded area to remove the ends of the elongate element or band distal to the fastened or welded area. Tension is applied to the ends of the elongate element or band 20d after the elongate element is looped around the posts of the anchors 10b, d. Applying tension to the elongate element 20d presses the anti-adhesion cover 18 in place against the spine and prevents migration of the anti-adhesion cover 18. The longitudinal fixation component also further inhibits or limits motion between the cranial and intermediate vertebrae. The method is advantageous in that it is much quicker and easier than prior methods which required threading one or more sutures through small openings in the anti-adhesion cover 18 to hold it in place. Moreover, this method eliminates the risk of the sutures cutting through the anti-adhesion component due to tension on the anti-adhesion component and allowing the anti-adhesion component to migrate away from the spine.

As shown in FIG. 2C, folding over flap 18' results in complete coverage of the in growth component 15, elongate elements 20a-d and anchors 10a-d, thereby preventing adhesions to the elongate elements or bands, in-growth component, and the anchors and preventing injury to delicate structures such as nerves, blood vessels, and the esophagus that lie directly over the anchors.

Figure 2D:
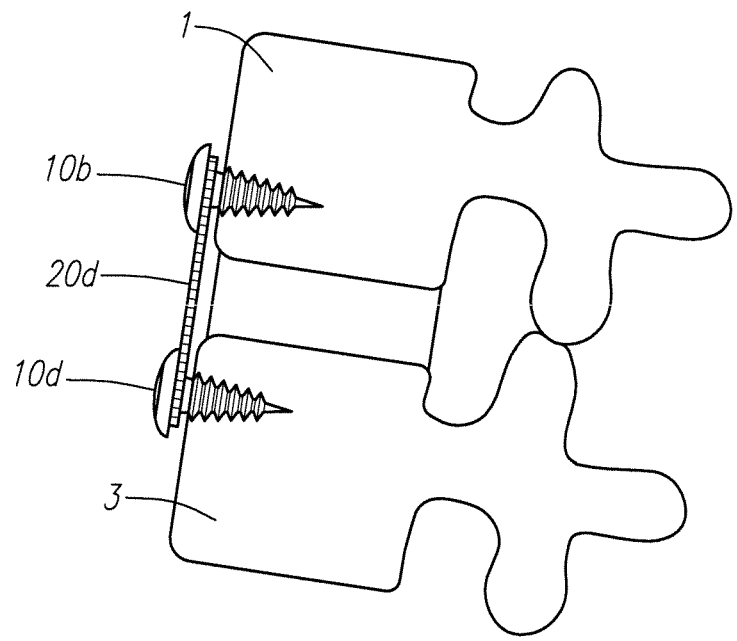
FIG. 2D is a lateral view of a sagittal cross section of the embodiment in FIG. 2C.

FIG. 2D is a lateral view of a partial sagittal cross section of a portion of the spine and the embodiment of the invention. Elongate element or suture band 20d connects the two anchors 10b, d. The in-growth component (not shown) can be positioned in an area between the anchors 10b,d. An anti-adhesion component (not shown) can be positioned over the in-growth component, anchors 10b,d, and elongate elements 20d.

Figure 2E:
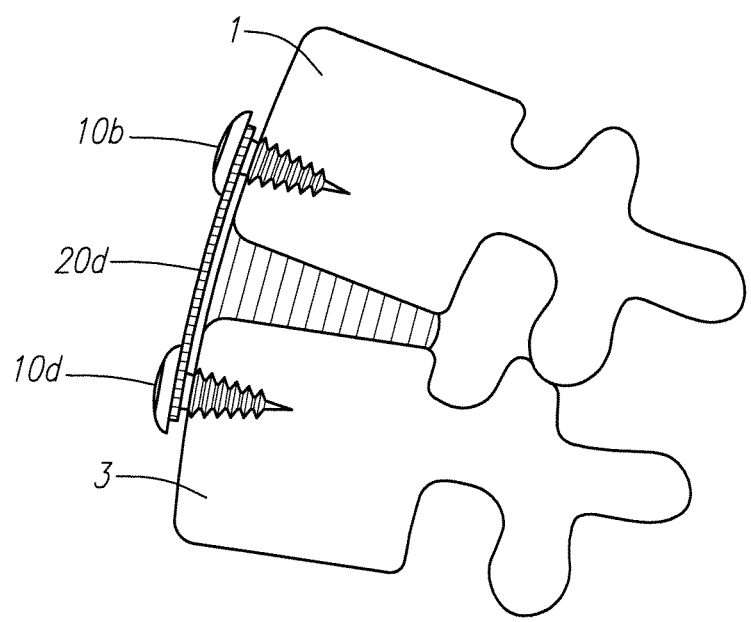
FIG. 2E is a lateral view of the sagittal cross section of the embodiment in FIG. 2D.

FIG. 2E is a lateral view of a partial sagittal cross section of a portion of the spine and the embodiment of the invention drawn in FIG. 2D. Anchors 10b, d were advanced further into vertebrae 1,3 after placement of elongate element or suture band 20d. Advancing the anchors reduces the profile of the device. Advancement of diverging anchors could also be performed to increase tension on the suture bands.

Figure 3A:
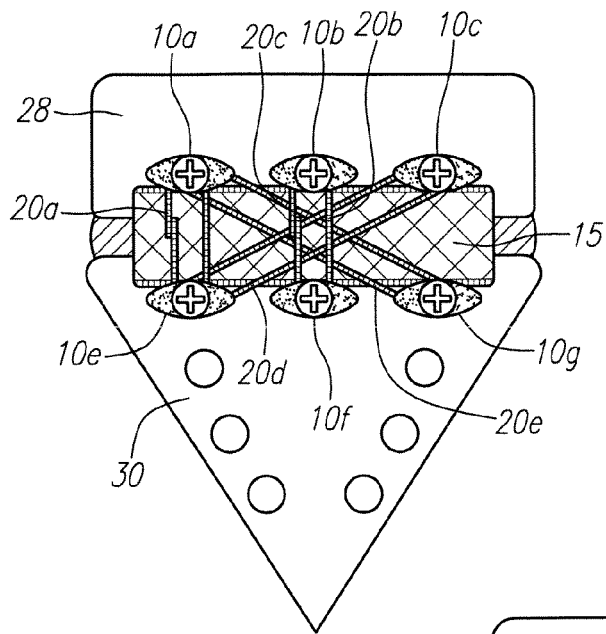
FIG. 3A is an anterior view of an alternative embodiment for stabilizing the lumbosacral junction of the spine.

FIG. 3A is an anterior view of the lumbosacral junction of the spine and an alternative embodiment of the invention. Sacrum 30 is located at the bottom of the spine and lies between the fifth lumbar segment 28 and the coccyx (tailbone). The sacrum comprises 4-5 vertebral bones that are fused into a wedge-shape. The anterior surface is typically smooth and concave. The elongate elements 20a-e connect six anchors 10a-g. Anchors 10a-c were inserted into lumbar vertebra 28 and anchors 10e-g were inserted into sacrum 30. In-growth component 15 lies between anchors 10a-g and adjacent the anterior surface of the spine. Elongate element or band 20a connects anchors 10a,e on the right side of the spine. Elongate elements or bands 20b,c connect anchors 10b,f in the center of the vertebrae. Elongate element or band 20d connects anchor 10e in the right side of sacrum 30 to anchor 10c in the left side of cranial vertebra 28. Elongate element or band 20e connects anchor 10g in the left side of sacrum 30 to anchor 10a in the right side of cranial vertebra 28.

In-growth component 15 lies between the elongate elements and the spine. In some embodiments, the in-growth component can comprise a mesh patch. The mesh patch may be made of synthetic materials such as polyester, polypropylene, ePTFE, or polyethylene. Alternatively, the mesh could be made of natural material such as autograft, allograft, or xenograft tissues such as acellular dermis, swine intestinal submucosa, ligaments, facia, or tendon. The mesh patch is preferably about 0.25 mm thick. Alternatively, mesh patch may be about 0.1 to about 2.0 mm thick. The mesh preferably has 1 by 1 mm pores. Alternatively, the mesh may have pores about 0.001 by about 0.005 mm in size to about 1 by about 3 mm in size. The holes in the mesh may be circular or elongate in shape and are preferably sized to promote tissue in-growth. The mesh component is preferably supplied in various sizes to fit in between the adjacent anchors. As shown in FIG. 3A, in some embodiments, the cranial and caudal sides of the in-growth component 15 have small slits. The slits are preferably about 2 to about 4 mm long. Alternatively, the slits could be about 1, about 5, about 6, about 7, or more millimeters long. The invention enables a piece of mesh to be press fit between the anchors. The anchors do not pass through the in-growth component rather small tab-like portions of the mesh fold along the anchors allowing the remaining portion of the mesh lies flat against the spine without wrinkles.

Elongate elements 20a-e are placed over the in-growth component 15 such that tension applied to the elongate elements 20a-e will press the in-growth component 15 against the spine preventing the in-growth component from migrating and promoting tissue in-growth. Tension across elongate elements 20a-e also prevents lateral bending, extension, and rotation of the lumbosacral junction. In alternate embodiments, the elongate elements 20a-e can be arranged in any combination of vertical and diagonal patterns between anchors 10a-f to hold the in-growth component against the spine and to apply tension across the lumbosacral junction.

Figure 3B:
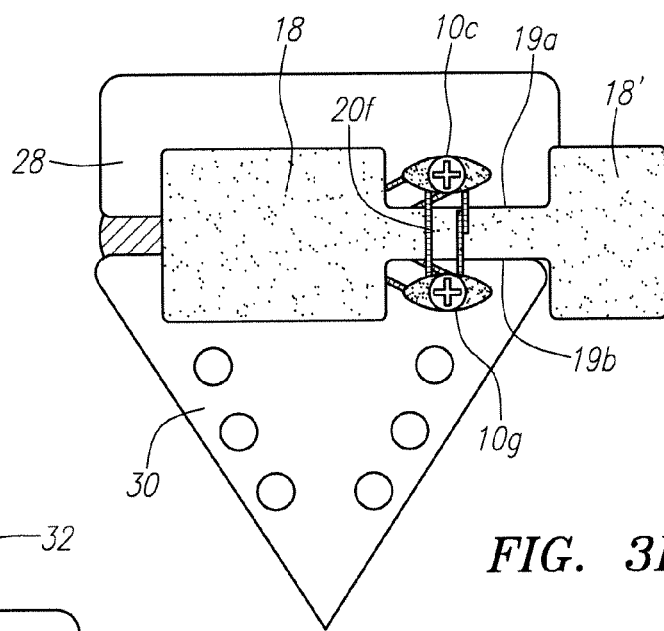
FIG. 3B is an anterior view of the embodiment in FIG. 3A illustrating the anti-adhesion component with notches exposing at least two anchors and an elongate member placed over the anti-adhesion cover and connecting the exposed anchors.

FIG. 3B is an anterior view of the lumbosacral junction of the spine and the embodiment of the invention drawn in FIG. 3A with an anti-adhesion component 18 covering the in-growth component 15 and many of the anchors 10a,b,e,f and elongate elements 20a-d. The anti-adhesion component 18 comprises a rectangular patch with a width and length sufficient to extend beyond the in-growth component 15, elongate elements or bands 20a-d and anchors 10a-g. At least two notches or openings 19a,b have been made in the anti-adhesion patch 18 to expose at least two anchors 10c, g to enable placement of an elongate element 20f or band therebetween. A flap 18' sized to completely cover the openings 19a,b extends from between the openings 19a,b. As discussed above, the anti-adhesion cover 18 is made of a material that discourages tissue in-growth or adhesions. For example, anti-adhesion cover 18 may be made of ePTFE, Sepratfilm, allograft, or absorbable materials. These absorbable materials include oxidized atelocollagen type I, polyethylene glycol, glycerol, or combinations thereof. In addition, anti-adhesion cover 18 will preferably have interstitial pore sizes of 3 microns or less to discourage tissue in-growth.

In use, anti-adhesion component 18 is placed over the elongate elements or bands 20*a-d*, in-growth component 15, and anchors 10*a-g* such that anchors 10*c,g* remain exposed via notches 19*a,b*. An additional elongate element or band 20*f*, such as a suture band, is placed around the post of anchor 10*b* in the left side of the lumbar vertebrae 28 and the post of anchor 10*d* in the left side of the sacrum 30. The ends of the elongate element or band 20*f* are fastened, preferably by ultrasonic welding, in the tightened configuration. The elongate element or band 20*f* is cut just distal to the fastened or welded area to remove the ends of the elongate element or band distal to the fastened or welded area. Tension is applied to the ends of the elongate element or band 20*f* after the elongate element is looped around the posts of the anchors 10*b, d*. Applying tension to the elongate element 20*f* presses the anti-adhesion cover 18 in place against the spine and prevents migration of the anti-adhesion cover 18. The longitudinal fixation component also further inhibits or limits motion in the lumbosacral junction. The method is advantageous in that it is much quicker and easier than prior methods which required threading one or more sutures through small openings in the anti-adhesion cover 18 to hold it in place. Moreover, this method eliminates the risk of the sutures cutting through the anti-adhesion component due to tension on the anti-adhesion component and allowing the anti-adhesion component to migrate away from the spine.

Figure 3C:
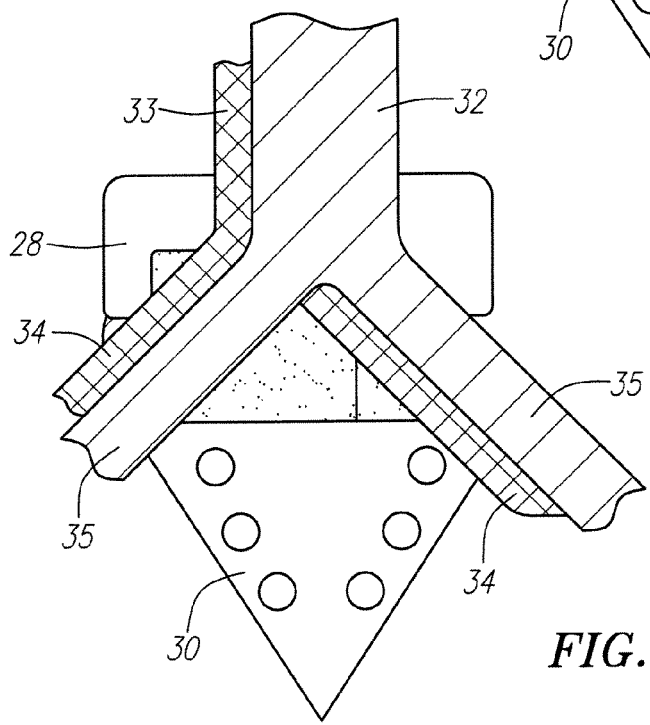
FIG. 3C is an anterior view of the embodiment in FIG. 3B illustrating the overlying anatomy.

FIG. 3C is an anterior view of the lumbosacral spine, the embodiment of the invention drawn in FIG. 3B and the overlying anatomy, which includes the great vessels (aorta 32, vena cava 33, iliac veins 34, and iliac arteries 35). Folding over flap 18' results in complete coverage of the in growth component 15, elongate elements 20*a-f* and anchors 10*a-g*, as seen in FIG. 3C thereby preventing adhesions to the elongate elements or bands, in-growth component, and the anchors and preventing injury to great vessels that lie directly over the anchors.

Figure 4A:
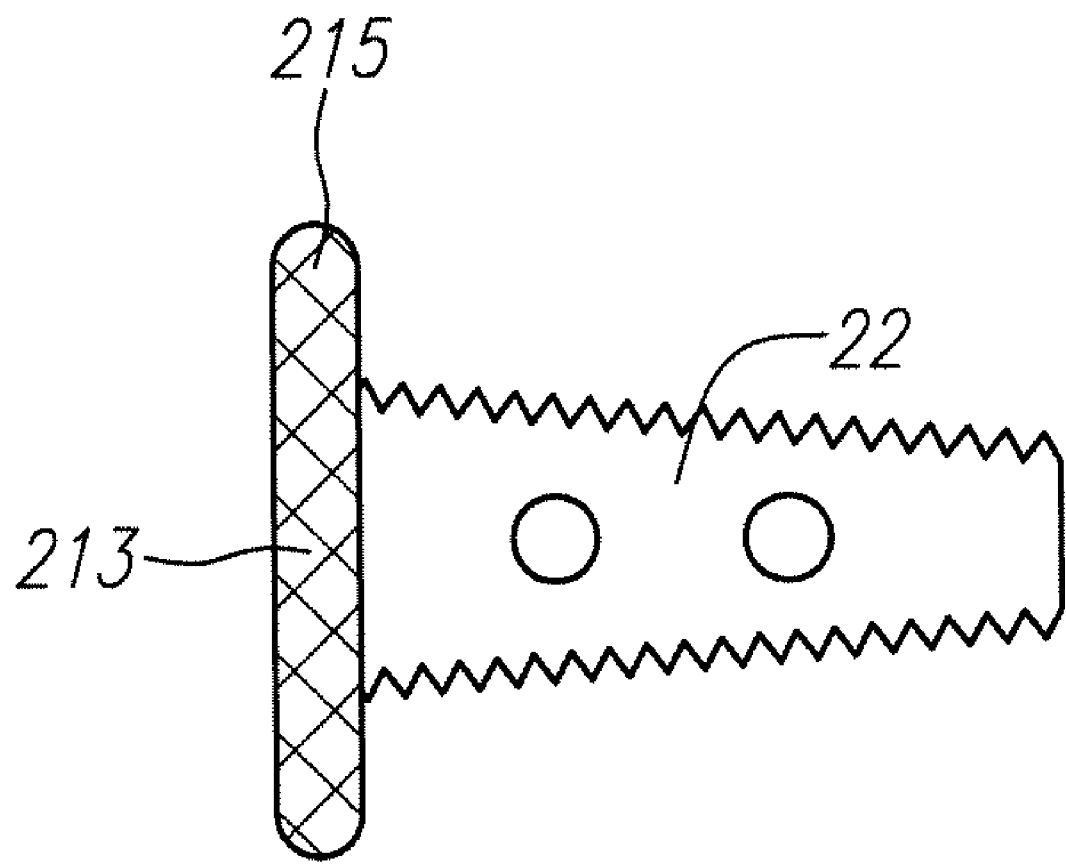
FIG. 4A is a lateral view of an embodiment of an intradiscal cage.

FIG. 4A is a lateral view of an alternative embodiment of an intradiscal cage that can be used in the above described embodiments. Intradiscal device 12 has a trapezoidal shape. As stated previously, the trapezoidal shape helps preserve the natural lordosis of the spine, which is the normal inward curvature of the lower region of the spine resulting in a concave back as viewed from the side. The intradiscal devices are preferably sized to fill the entire disc space. A mesh in-growth component 215 has been fastened to the anterior surface of the cage 12. A small screw 213, with a washer 217, could be used to fasten the mesh in-growth component 215 to the intradiscal component 12. Alternative mechanisms could be used to fasten the components. For example, the components could be connected with rivets, deformable plastic components, adhesives or other mechanism. Mesh could also be fastened to the anterior portions of other intradiscal devices such as bone grafts, nucleus replacements, total disc replacements, or other devices.

Figure 4B:
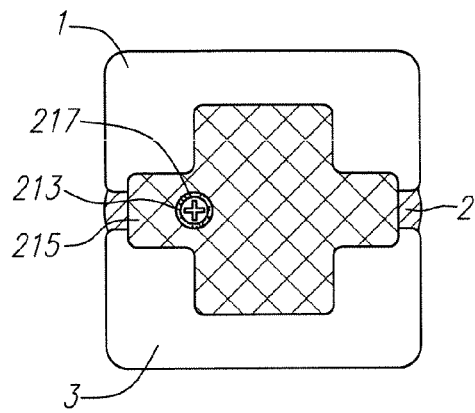
FIG. 4B is an anterior view of a portion of the spine illustrating the embodiment of FIG. 4A placed in the disc space between two adjacent vertebrae.

FIG. 4B is an anterior view of a portion of the spine and the embodiment of the invention drawn in FIG. 4A. The cage 12, or other intradiscal device, has been placed into the disc space. The mesh component 215 extends over the anterior portions of the vertebrae 1, 3 and the disc 2.

Figure 4C:
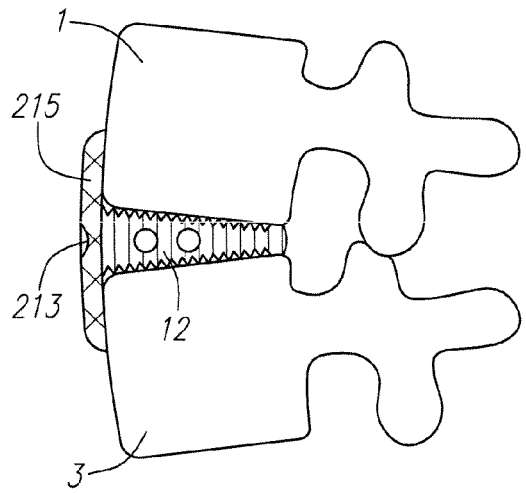
FIG. 4C is a sagittal cross-section of the embodiment in FIG. 4B.

FIG. 4C is a partial sagittal cross section of a portion of the spine and the embodiment of the invention drawn in FIG. 4B. The cage 12 holds the mesh 215 over the anterior portion of the spine.

Figure 4D:
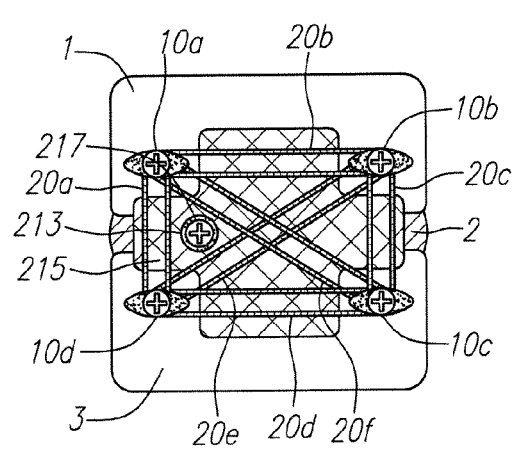
FIG. 4D is an anterior view of the embodiment in FIG. 4C illustrating elongate bands connecting anchors in the two adjacent vertebrae to hold the mesh component in place.

FIG. 4D is an anterior view of a portion of the spine, the embodiment of the invention drawn in FIG. 4B with suture bands connecting the anchors. Screws 10*a-d* and suture bands 20*a-f* may be applied over the mesh 215 such that tension applied to the suture bands 20*a-f* will press the in-growth component against the spine promoting tissue in-growth. The embodiment includes additional horizontal bands 20*b, d*. The bands between the screws in the same vertebra (i.e., the horizontal bands) hold the mesh firmly against the vertebra. As discussed above with regard to the embodiments shown in FIGS. 1-3, an anti-adhesion component (not shown) may be used to cover the bands, in-growth component, and anchors.

Figure 5A:
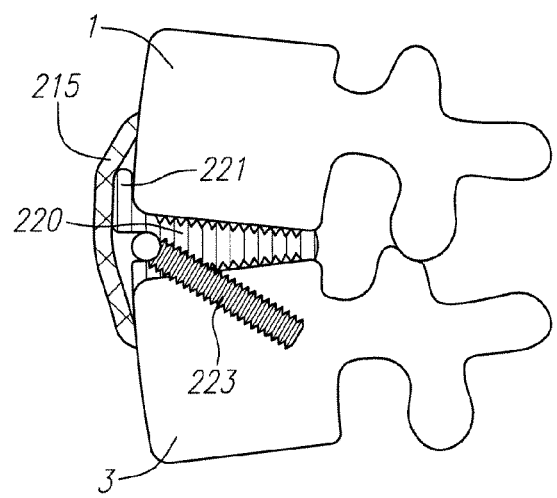
FIG. 5A is sagittal cross-section of an alternative intradiscal cage.
Figure 5B:
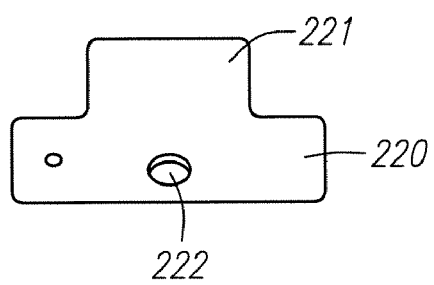
FIG. 5B is an anterior view of the intradiscal cage in FIG. 5A.

FIG. 5A is a partial sagittal cross section of a portion of the spine and an alternative intradiscal cage that can be used in the above described embodiments. FIG. 5B is an anterior view of the cage drawn in FIG. 5A. Intradiscal cage 220 has a generally trapezoidal shape, a lip 221 extending from the anterior portion of the cranial end of the cage, and hole or opening 222 adapted to receive a screw or anchor therethrough. The lip 221 is positioned against the anterior portion of the vertebra. One or more screws 223 are passed through the cage 220 and into the vertebra caudal 3 to the device. Alternatively, the lip 221 could extend anterior to the caudal vertebra 3 and one or more screws 223 directed into the cranial vertebra 1. Alternatively, one or more screws could be directed into cranial vertebra 1 and caudal vertebra 3. The invention resists translation of one vertebra relative to the second vertebra.

Figure 6A:
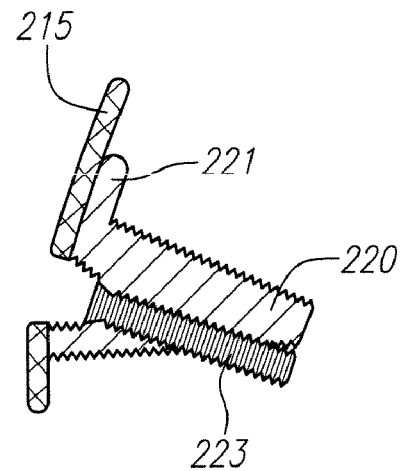
FIG. 6A is a sagittal cross-section of an alternative embodiment of the intradiscal cage in FIG. 5A.

FIG. 6A is a sagittal cross section through an alternative embodiment of the invention drawn in FIG. 5A. The screw 223 is threaded into the cage 220 and the vertebra. Two or more threads, of the same pitch as the threads on the distal portion of the screw, are chanced onto the head of the screw. The configuration helps lock the screw 223 into the cage 220.

Figure 6B:
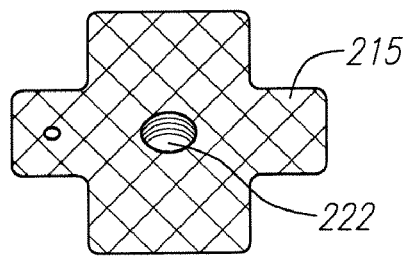
FIG. 6B is an anterior view of the intradiscal cage in FIG. 6A with an in-growth component attached to the cage.

FIG. 6B is an anterior view of the embodiment of the invention drawn in FIG. 6A. In-growth mesh component 215 is attached onto the front of the cage.

Figure 10A:
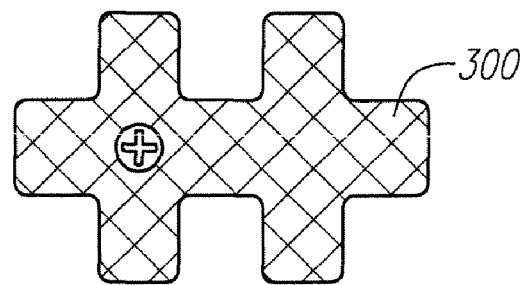
FIG. 10A is an anterior view of an alternative intradiscal device.

FIG. 10A is an anterior view of an alternative intradiscal device. In-growth component 315 is shaped for insertion between the area defined by six anchors, three anchors into the vertebra cranial to the device and three anchors into the vertebra caudal to the device. In-growth component 315 has four elongate extensions, wherein two elongate extensions extend from opposite sides of a central elongate member. The open spaces on either side of the extensions and between the side-by-side extensions are adapted for placement of the anchors. The mesh component 315 is preferably about 10-20 mm wide and about 10-24 mm tall for embodiments of the invention for the cervical spine. Alternatively the mesh component 315 could be about 9, about 8, or about 7 mm or smaller in width or height and about 21, about 22, about 23, about 25, or about 26 mm, or larger in width or height. The mesh is preferably about 20-50 mm wide and about 20-50 mm tall for embodiments of the invention for the lumbar spine. Alternatively, the mesh component 315 could be about 19, about 18, or about 17 mm or smaller in height or width and about 51, about 52, or about 53 mm or larger in width or height. The shape of the mesh helps surgeons determine the optimal location to place the anchors. Alternatively, the device could be used without anchors and longitudinal fixation members. The intradiscal device could have an in-growth patch made of materials such as polyester mesh, polypropylene and an anti-adhesion cover. An anti-adhesion cover (not shown) could be sized to cover the in-growth component, anchors, and/or elongate elements or bands, and could be made of materials such as ePTFE. The anti-adhesion cover may also be attached to the intradiscal device. Lastly, the patch on the intradiscal device may be limited to in-growth or anti-adhesion materials.

Figure 10B:
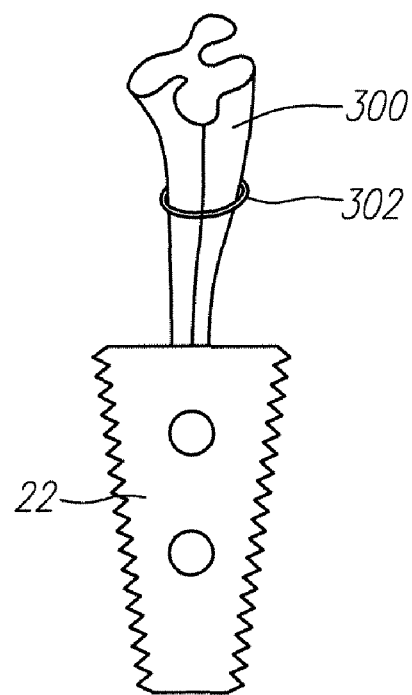
FIG. 10B is a lateral view of the embodiment in FIG. 10A illustrating the in-growth component in a folded configuration.

FIG. 10B is a lateral view of the embodiment of the invention drawn in FIG. 10A. The patch (in-growth component 300 and/or anti-adhesion component (not shown)) on the anterior portion of the intradiscal cage 22 has been folded and lifted away from the anterior surface of the cage 22. A band or tie 302 holds the patch 300 in the folded configuration. The invention helps surgeons see all the edges of the cage while they are inserting the cage 22 into the disc space. Alternatively, the folded patch 300 could be temporarily inserted into the lumen of a tool used to insert the intradiscal device.

Devices in Other Bones and Ligaments

Figures 7A, 7B:
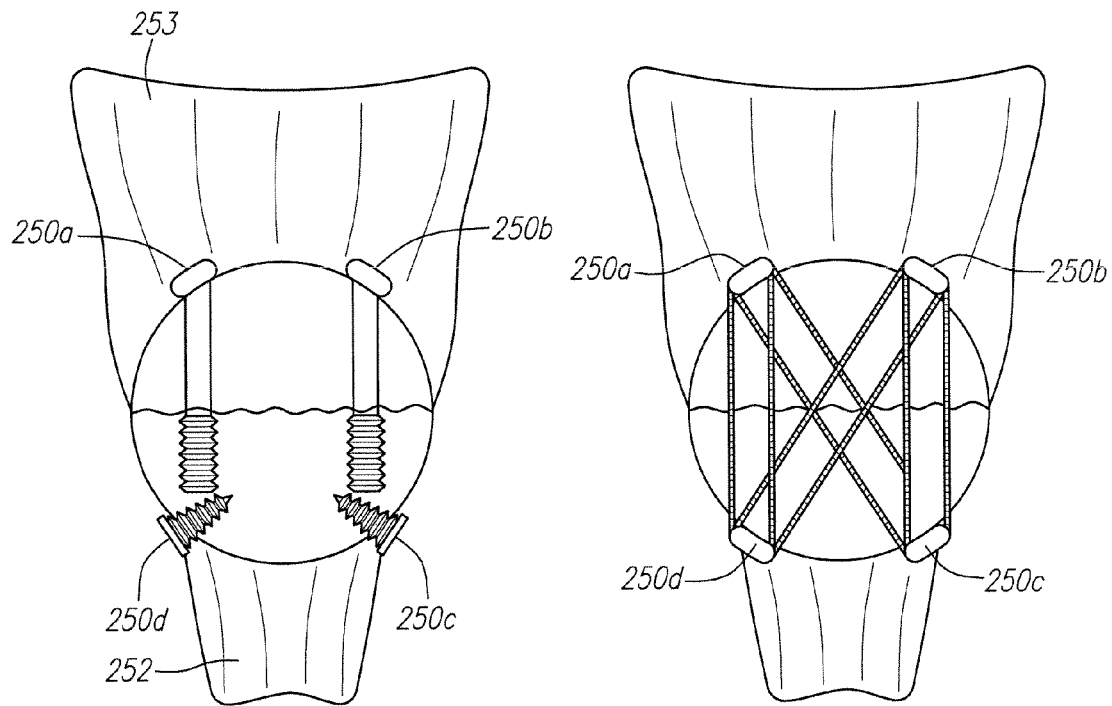
FIG. 7A is an anterior view of a coronal cross-section of the patella illustrating an alternative embodiment for reconstructing a fracture in the patella.
FIG. 7B is an anterior view of the embodiment in FIG. 7A illustrating suture bands connecting the anchors.

FIG. 7A is an anterior view of coronal cross section of the patella, the patella tendon 252 (distal to the patella), a portion of the quadriceps muscle 253, and an alternative embodiment of the invention. Two screws 250a-d have been inserted across a transverse fracture in the patella. Two screws have been placed into the distal pole of the patella.

FIG. 7B is an anterior view of the patella, the patella tendon, a portion of the quadriceps muscle with bands connecting the anchors.

Figures 8A, 8B:
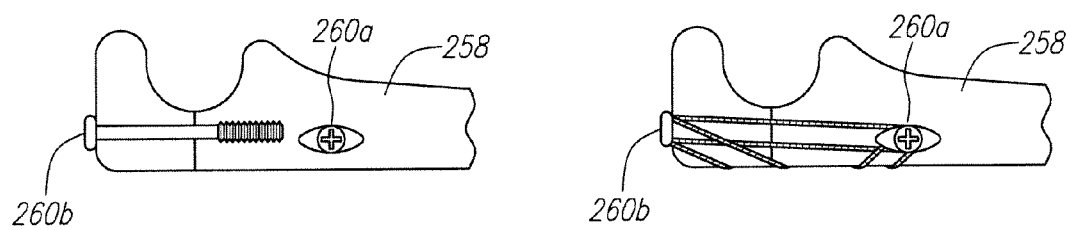
FIG. 8A is a lateral view of a sagittal cross-section of the ulna illustrating an alternative embodiment for reconstructing a fracture in the ulna.
FIG. 8B is a lateral view of the embodiment in FIG. 8A illustrating suture bands connecting the screws.

FIG. 8A is a lateral view of a sagittal cross section through the proximal ulna 258 with anchors disposed therethrough. FIG. 8B is a lateral view of the proximal portion of the ulna and the embodiment of the invention drawn 8A.

Figure 8C:
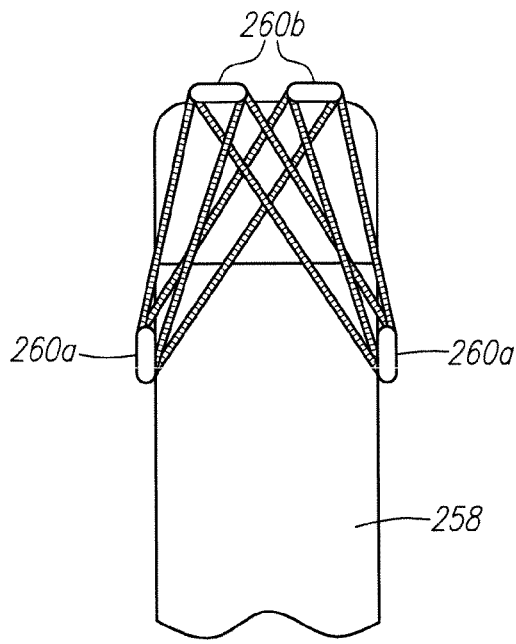
FIG. 8C is a posterior view of the embodiment in FIG. 8B.

FIG. 8C is posterior view of a portion of the ulna and the embodiment of the invention drawn in FIG. 8B. The invention may be used to treat fractures of the other bones of the axial skeleton or the extremities. Bands were applied over the screws in the manner taught previously. Two screws 260a,b have been inserted across a fracture through the olecranon. Screws 260a,b have also been inserted into the ulna distal to the fracture. The screws are preferably placed in different planes to minimize the stress risers from the holes in the bone.

Figure 9A:
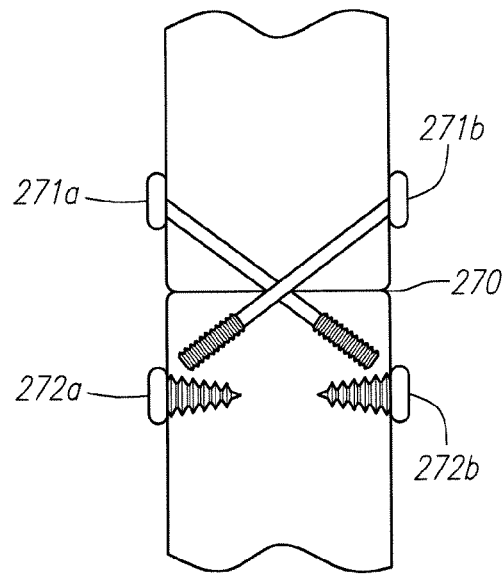
FIG. 9A is a coronal cross-section through a joint between two bones illustrating an alternative embodiment for fusing a joint.

FIG. 9A is a partial coronal cross section through a joint between two bones and an alternative embodiment of the invention. Two screws 271a,b have been placed across the joint 270. Screws 272a,b were also placed in the bone of the distal half of the joint 270.

Figure 9B:
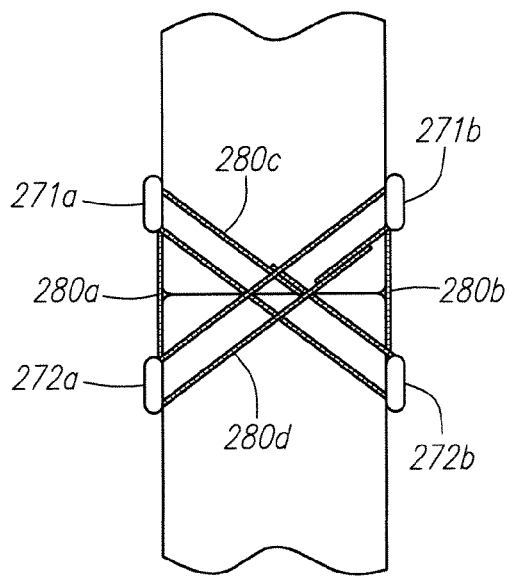
FIG. 9B is a posterior view of the embodiment in FIG. 9A illustrating suture bands connecting the screws.

FIG. 9B is a posterior view of the joint and embodiment of the invention drawn in FIG. 9A. Bands 280a-d have been applied around the screws. The invention may be used to fuse joints in the axial skeleton or the extremities. The invention is particularly useful for fusing the joints of the hand or foot.

Figure 11A:
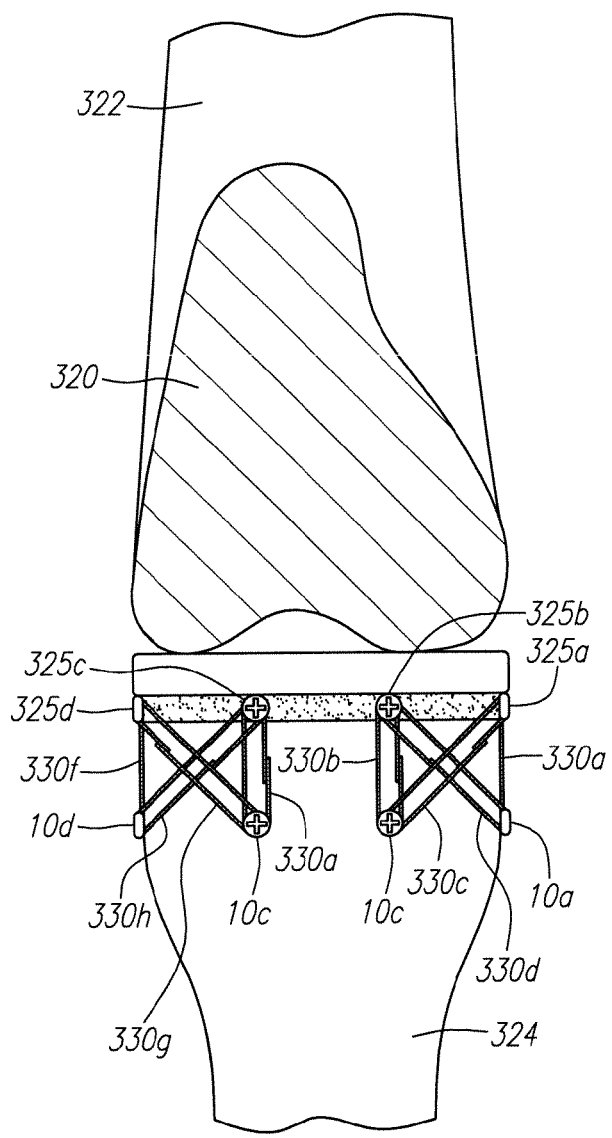
FIG. 11A is an anterior view of an alternative embodiment for attaching a prosthetic knee.

FIG. 11A is an anterior view of a prosthetic knee 320, a portion of the femur 322, a portion of the tibia 324 and an alternative embodiment of the invention. Anchors 10a-d, as previously described, were inserted into the anterior, medial, and lateral portions of the proximal tibia 324. T-shaped projections 325a-d extend from the anterior, medial, and lateral portions of the tibial portion of the knee replacements. Suture bands 330a-h were placed over the T-shaped projections 325a-d and the anchors 10a-d. Tension on the bands 330a-h compresses the tibial component of the prosthetic knee 320 against the tibia 324. The invention facilitates bone in-growth into the tibial component. The invention also reduces movement between the tibial component and the tibia 324. The t-shaped members 325a-d, the anchors 10a-d, and/or the sutures 330a-h may be resorbable. One or more resorbable component reduces the risk of particle debris. The resorbable component ideally maintains its ability to resist the forces applied to the component for at least two to three months.

Figure 11B:
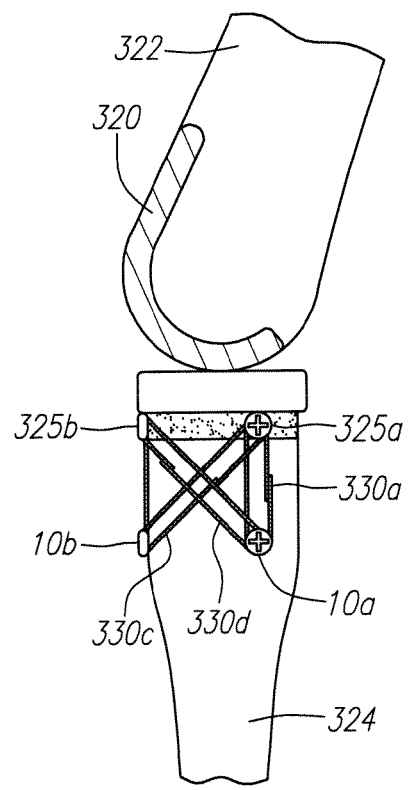
FIG. 11B is a lateral view of the embodiment in FIG. 11A.

FIG. 11B is a lateral view of the prosthetic knee 320, a portion of the femur 322, a portion of the tibia 324, and the embodiment of the invention drawn in FIG. 12A. The invention could be used to fasten other prosthetic components of other parts of the body including other bones.

Anchors

FIG. 12A is an exploded lateral view of an anchor suitable for use in the above described embodiments. Anchor 40 has a first portion 41 adapted to be inserted into bone and an enlarged end or head 42. The first portion may further comprise threads 43. Washer-like component 44 is adapted to be threaded onto the screw.

FIG. 12B is a lateral view of the embodiment of the invention drawn in FIG. 12A. Washer-like component 44 is partially threaded onto the first portion 41 of screw 40. The hole in the center of washer-like component 44 is larger than the internal diameter of the first portion 41 of screw 40 and preferably smaller than the outer diameter of threads 43 of the screw such that it can be rotated and advanced up the threads to sit adjacent the enlarged head of the screw.

FIG. 12C is a lateral view of the embodiment of the invention drawn in FIG. 12B. Washer-like component 44 lies beneath the head 42 of the screw. The washer may rotate around the shaft 41 of the screw. In one embodiment, the shaft of the screw preferably has a slight taper just below the head of the screw. The diameter of the shaft 41 just below the head of the screw is slightly smaller than the diameter of the screw approximately 1 to 3 millimeters above the threads of the screw. Washer-like component 44 is forced into the tapered portion of the shaft of the screw. This configuration helps keep the washer-like component near the head of the screw. Alternative configurations could be used to keep the washer-like component close to the head of the screw. For example, the shaft of the screw may have a small raised area about 2 to 5 millimeters below the head of the screw. The washer-like component could be forced over the projection. The projection helps hold the washer-like component near the head of the screw. Alternatively, the washer-like component could have an opening on the side of the component. The U or C shaped component could be snapped into a recessed area just below the head of the screw.

Figure 12E:
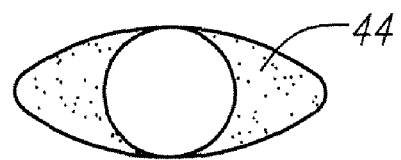
FIG. 12E is a view of the top of the washer-like component drawn in FIG. 12A.
Figure 13A:
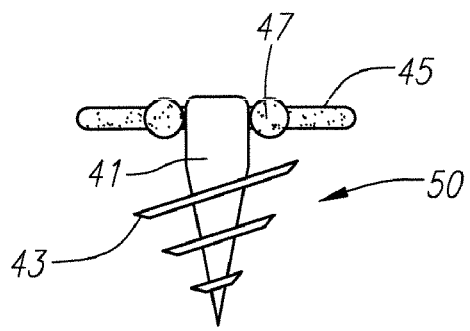
FIG. 13A is a lateral view of an alternative anchor having an elongate transverse component at the end of the screw.
Figure 13B:
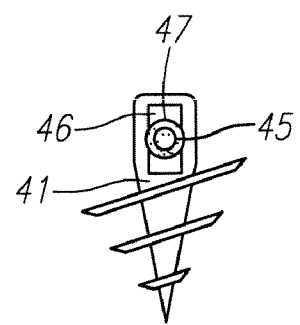
FIG. 13B is an anterior view of the embodiment of the invention drawn in FIG. 13A.
Figure 13C:
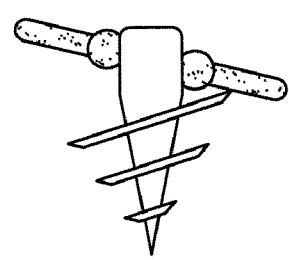
FIG. 13C is a lateral view of the embodiment of the invention drawn in FIG. 13A.

FIG. 12D is an anterior view of the embodiment of the invention drawn in FIG. 13C. Washer 44 has an elongate shape. As seen from the anterior view, the width of the washer is approximately the same width or diameter as the enlarged end or head of the anchor 40. The smooth area of the screw below the washer and above the first thread is preferably about 2 to about 6 mm long. Alternatively, such area could be about 1 mm or less long or about 7, about 8, or about 9 mm or more long. The smooth area between the washer and the first thread may have one or more ridges around the circumference of the screw. The ridges may be used to separate the suture bands. For example, one ridge may be used to separate the ends of two suture bands. Two ridges may be used to separate the ends of three suture bands. Three ridges may be used to separate the ends of four suture bands. Alternatively, one ridge could be used to separate the ends of four suture bands, if the ends of two or more suture bands are contained on either side of the ridge. The edges of the ridge should be rounded to avoid damaging the sutures. The ridges are preferably about 1 to about 4 mm tall. Alternatively, the ridges may be less than about 1 mm tall or about 5, about 6, or about 7 mm or more tall.

FIG. 12E is a view of the top of the washer-like component drawn in FIG. 12A. The component is elongated. The ends of the component are preferably tapered. The component is preferably between about 3 mm and about 7 mm long. Alternatively, the component could be about 2, about 8, about 9, about 10, or more millimeters long. The hole in the component preferably has a diameter of about 2 mm. Alternatively, the hole could have a diameter of about 1, about 3, about 4, or more millimeters. The component is preferably about 3 mm to about 6 mm wide. Alternatively, the component may be about 1, about 2, about 7, about 8, about 9, or more millimeters wide.

Figure 12F:
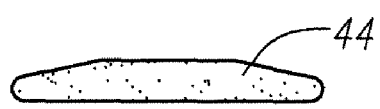
FIG. 12F is a lateral view of the embodiment of the invention drawn in FIG. 12E.
Figure 12G:
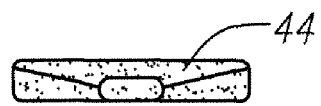
FIG. 12G is an anterior view of the embodiment of the invention drawn in FIG. 12F.

FIG. 12F is a lateral view of the embodiment of the invention drawn in FIG. 12E. Washer component 44 is preferably thinner about the periphery of the component than at the center of the component. The center of component 44 is preferably about 1 mm to about 3 mm thick. Alternatively, the center of the component may be less than about 1 millimeter thick, alternatively less than about 4, alternatively less than about 5, alternatively less than about 6, or more millimeters thick. FIG. 12G is an anterior view of the embodiment of the invention drawn in FIG. 12F.

Figure 19A:
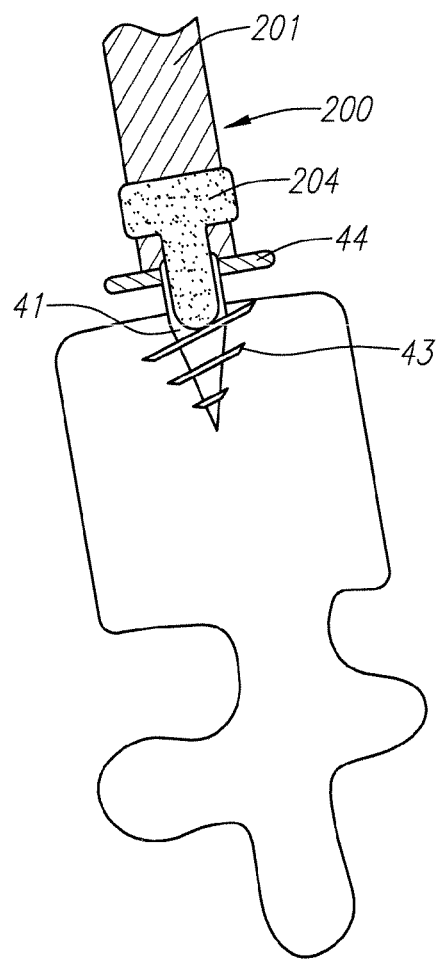
FIG. 19A is a partial sagittal cross section of a vertebra with a screwdriver being used to insert an anchor having a threaded portion and a washer.

FIG. 19A is a partial sagittal cross section of a vertebra with a screwdriver being used to insert an anchor having a threaded portion and a washer. Screwdriver 200 has an elongate member with a Philip's screwdriver head 202 (or a regular screwdriver head) at the distal end and sleeve 201 disposed about the shaft of the screw driver and having projections 204 disposed about and extending beyond the distal end of sleeve 201. The projections 204 from the distal end of the sleeve 201 over the tip of the screwdriver are designed to impinge against the vertebra, before the screw 40 is fully inserted into the vertebra. Preferably the invention allows all of the threads 43 of the screw to be advanced into the vertebra before the impingement occurs. The tool preferably leaves about 1 to about 3 mm between the washer 44 and the face of the vertebra. Alternatively the tool could leave less than about 1 mm or alternatively about 3, about 4, about 5 or more millimeters between the washer 44 and the bone. The space between the washer 44 and the bone facilitates application of the suture bands around the shaft of the screw. The screw can be advanced until the washer impinges against the bone, after application of all the bands.

Figure 19B:
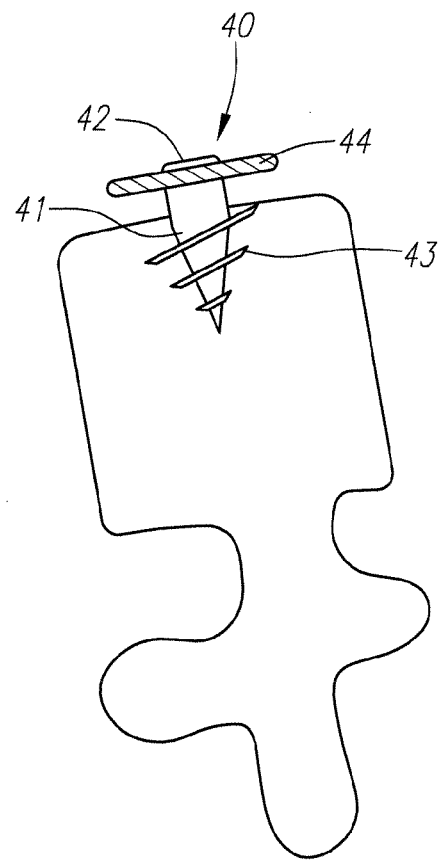
FIG. 19B is a partial sagittal cross section of a vertebra and the screw.

FIG. 19B is a partial sagittal cross section of a vertebra and the screw. The drawing illustrates space between the washer 44 and the vertebra.

Figure 19C:
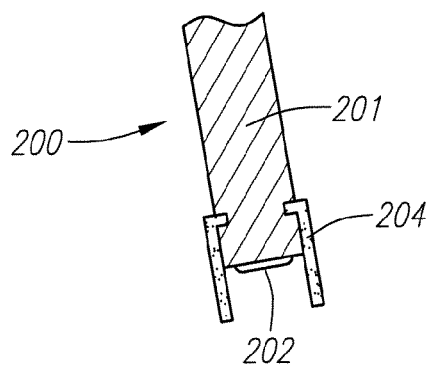
FIG. 19C is a sagittal cross section of the end of the screwdriver 200 drawn in FIG. 19A.

FIG. 19C is a sagittal cross section of the end of the screwdriver 200 drawn in FIG. 19A. The sleeve 201 may rotate about the shaft of the screwdriver. The configuration allows rotation of the screw without rotating the washer 44.

FIG. 13A is a lateral view of an alternative anchor having an elongate transverse component at the end of the screw. FIG. 13B is an anterior view of the embodiment of the invention drawn in FIG. 13A. Shaft 41 of the screw has a slot or lumen extending through a top portion. Elongate, transverse member 45 is disposed within the lumen.

FIG. 13C is a lateral view of the embodiment of the invention drawn in FIG. 13A. The elongated component may swivel in the slot of the screw component. Lumen 46 is larger/taller than the width of the elongate, transverse member 45, which allows the user to vary the angle of the elongate, transverse member 45 relative to the longitudinal axis of the shaft. The angle can vary from about 30 degrees to about 150 degrees, alternatively from about 45 degrees to about 135 degrees. Enlarged portions 47 along the length of elongate, transverse member 45 situated along the length of elongate, transverse member 45 on the portions just outside of the lumen of the shaft prevent the elongate member 45 from slipping out of lumen 46.

Figure 13D:
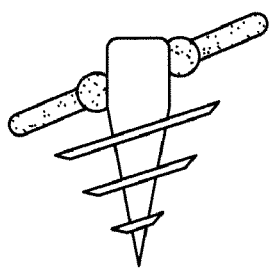
FIG. 13D is a lateral view of the embodiment of the invention drawn in FIG. 13C.

FIG. 13D is a lateral view of the embodiment of the invention drawn in FIG. 13C. The elongated component was swiveled in a different direction. The invention enables the device to be advanced into the vertebrae at angles other than perpendicular to the vertebrae. Swiveling of the elongated component prevents impingement of the tips of the elongated component as the screw is advanced into the vertebra at angles less than 90 degrees relative to the vertebrae.

Figure 13E:
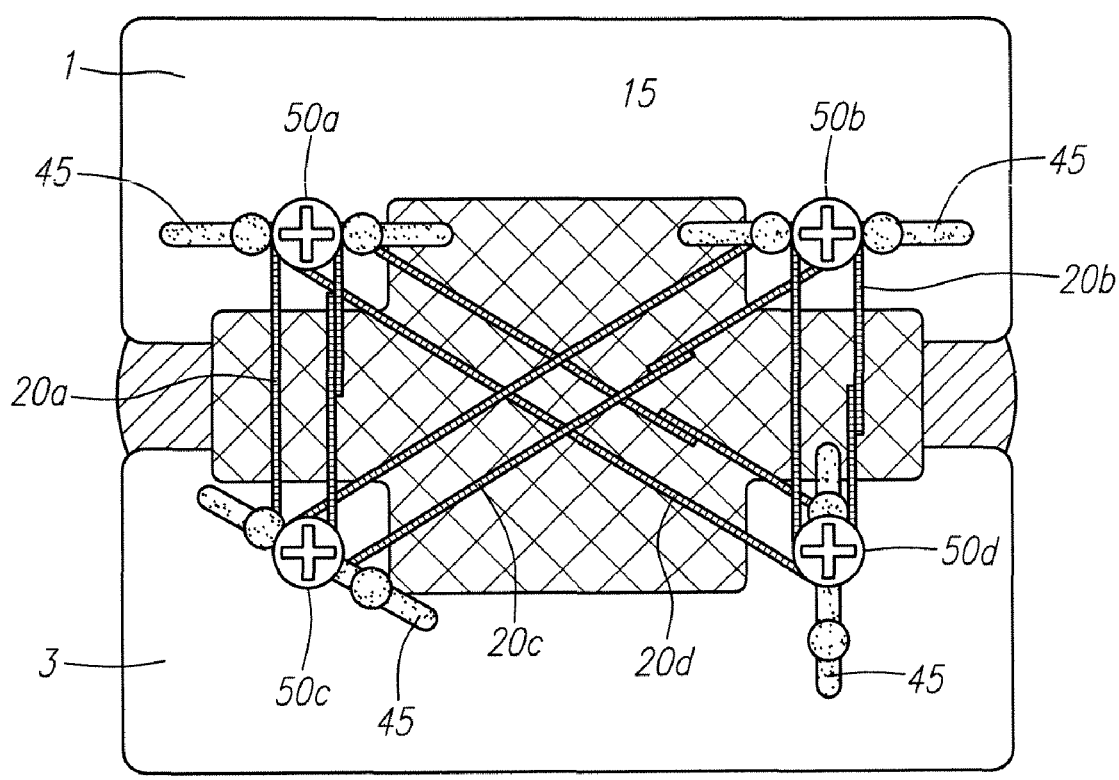
FIG. 13E is an anterior view of a portion of the spine and the embodiments of the invention drawn in FIGS. 2A and 13A.

FIG. 13E is an anterior view of a portion of the spine and the embodiments of the invention drawn in FIGS. 2A and 13A. Anchors 50a-d having the elongate transverse components 45 have been inserted into the cranial and caudal vertebrae 1, 3. In-growth component 15 has been placed adjacent the vertebra between the anchors. Elongate elements 20a-d connect anchors 50a-d.

Figure 13F:
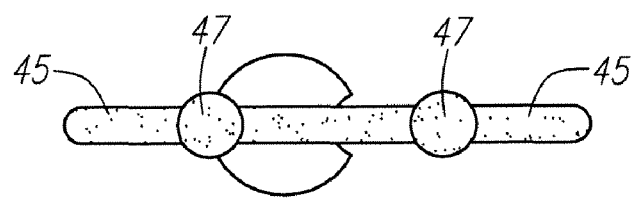
FIG. 13F is an axial cross section through the embodiment of the invention drawn in FIG. 13A.

FIG. 13F is an axial cross section through the embodiment of the invention drawn in FIG. 13A. Enlargements 47 along the elongated component and the slot within the screw cooperate to contain the elongated component in the screw. Enlargements 47 are preferable spherical. Alternatively, the enlargements may be oblong, rectangular, hemi-spherical or other shape. The sides of the slot in the screw preferably have concave surfaces. The articulating surfaces of the enlargements 47 of the elongated component 45 and the sides of the slot 46 are preferably congruent. Alternatively, such articulating surfaces may be non-congruent.

FIG. 14A is a lateral view of an alternative anchor. The central portion of the elongated component 45 has spherical enlargement 52. Spherical enlargement 52 of the elongated component 45 articulates in hole 46 through the shaft 41. The surfaces of the hole 46 through the screw are preferably concave.

FIG. 14B is a lateral view of the embodiment of the invention drawn in FIG. 14A. The elongated component has been rotated relative to the screw. As with the previous anchor, the shape of lumen 46 allows the user to vary the angle of the elongate, transverse member 45 relative to the longitudinal axis of the shaft. The angle can vary from about 30 degrees to about 150 degrees, alternatively from about 45 degrees to about 135 degrees. Spherical enlargement 52 also prevents the elongate member 45 from slipping out of lumen 46

FIG. 14C is a sagittal cross section through the embodiment of the invention drawn in FIG. 14A. Spherical enlargement 52 of elongated component is contained within the concave slot of the screw. The articulating surfaces of the components are preferably congruent. Alternatively, the articulating surfaces of the components may be non-congruent.

FIG. 15 is a sagittal cross section through an alternative anchor. In contrast to the spherical enlargement of FIG. 14, the top surface of enlargement 54 of the elongated component 45 was formed from a sphere with a smaller radius than the sphere used to form the bottom of the enlargement of the elongated component. This results in an anchor with a lower profile.

FIG. 16A is a lateral view of an alternative anchor. FIG. 16B is view of the top of the embodiment of the invention drawn in FIG. 16A. On one end, elongate component 58 is connected to shaft 41 through axle or hinge 56. On the other end, elongate component 58 is connected to transverse component 59, which is substantially perpendicular to the elongate component 58. Elongate component 58 may rotate about the hinge over the top of the shaft 180 degrees. Transverse component 59 may rotate 360 degrees around the end of the elongate component 58.

FIG. 17 is an anterior view of a portion of the spine and the embodiments of the invention drawn in FIGS. 2A and 16. Suture bands 20a-d are looped around the shafts of the elongate component 58. Transverse components 59 at the ends of elongate components 58 prevent the suture bands 20a-d from slipping, thereby holding in-growth component 15 in place.

Figure 18A:
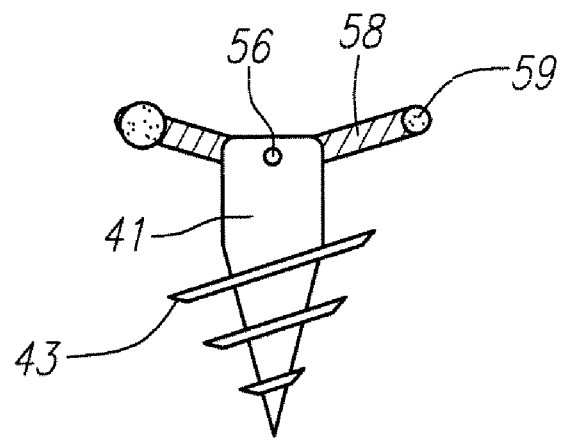
FIG. 18A is a lateral view of an alternative anchor having two arms connected by a hinge.
Figure 18B:
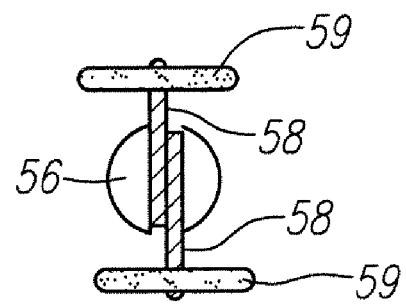
FIG. 18B is a view of the top the embodiment of the invention drawn in FIG. 18A.

FIG. 18A is a lateral view of an alternative anchor having two arms connected by a hinge. FIG. 18B is a view of the top the embodiment of the invention drawn in FIG. 18A. Axle or hinge 56 connects two T-shaped components (elongate component 58 and transverse component 59). As with the embodiment with one arm, elongate components 58 may rotate about the hinge over the top of the shaft 180 degrees, or alternatively 90 degrees. Transverse components 59 may rotate 360 degrees around the end of each elongate component 58.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for stabilizing a spinal segment comprising a first and a second vertebrae, the method comprising the steps of:
    providing first, second, third, and fourth anchors, wherein each anchor has a first portion adapted to be inserted into a vertebra and a second portion having an enlarged end;
    attaching the first and second anchors to the first vertebra;
    attaching the third and fourth anchors to the second vertebra, wherein the attachments of the first, second, third, and fourth anchors in the first and second vertebrae define an area;
    positioning an in-growth component over at least a portion of the first and second vertebrae, wherein at least a portion of the in-growth component lies within the area;
    connecting the first anchor and at least one of the third and fourth anchors with a first elongate element;
    connecting the second anchor and at least one of the third and fourth anchors with a second elongate element;
    applying tension to the first and second elongate elements such that the first and second elongate elements press at least a portion of the in-growth component against a portion of the first and second vertebra within the area;
    positioning an anti-adhesion cover over at least a portion of the area, wherein said anti-adhesion cover comprises a main portion, at least one opening positioned such that at least one of the first and second anchors and at least one of the third and fourth anchors are not covered by the main portion of the anti-adhesion cover, and a flap sized to completely cover said at least one first opening in the main portion;
    connecting the at least one uncovered first or second anchor and the at least one uncovered third and fourth anchor with a third elongate element, wherein the third elongate element holds at least a portion of the anti-adhesion cover within the area; and
    folding the flap of the anti-adhesion cover over the at least one opening in the main portion to cover the third elongate element, the at least one uncovered first or second anchor, and the at least one uncovered third and fourth anchor.

2. A method for stabilizing a spinal segment comprising first, second, and third vertebrae, the method comprising the steps of:
    providing first, second, third, fourth, fifth, and sixth anchors, wherein each anchor has a first portion adapted to be inserted into a vertebra and a second portion having an enlarged end;
    attaching the first and second anchors to the first vertebra;
    attaching the third and fourth anchors to the second vertebra;
    attaching the fifth and sixth anchors to the third vertebra, wherein the attachments of the first, second, third, fourth, fifth, and sixth anchors in the first, second, and third vertebrae define an area;
    positioning an in-growth component over at least a portion of the first, second, and third vertebrae, wherein at least a portion of the in-growth component lies within the area;
    connecting the first anchor and at least one of the third and fourth anchors with a first elongate element;
    connecting the third anchor and at least one of the fifth and sixth anchors with a second elongate element;
    connecting the fourth anchor and at least one of the fifth and sixth anchors with a third elongate element;
    connecting the first anchor and at least one of the fifth and sixth anchors with a fourth elongate element;
    connecting the second anchor and at least one of the fifth and sixth anchors with a fifth elongate element;
    applying tension to the first, second, third, fourth and fifth elongate elements such that the first, second, third, fourth and fifth elongate elements press at least a portion of the in-growth component against a portion of the first, second and third vertebrae within the area;
    positioning an anti-adhesion cover over at least a portion of the area, wherein the anti-adhesion cover has a main portion sized to substantially cover the area, at least one opening positioned such that at least two of the first, second, third, fourth, fifth, and sixth anchors are not covered by the main portion and a flap sized to substantially cover the at least one opening in the main portion;
    connecting the at least two uncovered first, second, third, fourth, fifth, and sixth anchors with a sixth elongate element;
    applying tension to the sixth elongate element such that the sixth elongate element holds at least a portion of the anti-adhesion cover within the area; and
    folding the flap over the at least one opening in the main portion to cover the third elongate element and the at least two uncovered first, second, third, fourth, fifth, and sixth anchors.

3. A method for stabilizing a spinal segment comprising a lumbar vertebra and the sacrum, the method comprising the steps of:
    providing first, second, third, and fourth anchors, wherein each anchor has a first portion adapted to be inserted into a vertebra and a second portion having an enlarged end;
    attaching the first and second anchors to the lumbar vertebra;
    attaching the third and fourth anchors to the sacrum, wherein the attachments of the first, second, third, and fourth anchors in the lumbar vertebra and sacrum define an area;
    positioning an in-growth component over at least a portion of the spinal segment, wherein at least a portion of the in-growth component lies within the area;
    connecting the first anchor and each of the third and fourth anchors with first and second elongate elements;
    connecting the second anchor and at least one of the third and fourth anchors with a third elongate element;
    applying tension to the first, second and third elongate elements such that the first, second, and third elongate elements press at least a portion of the in-growth component against a portion of the lumbar vertebra and the sacrum within the area;
    positioning an anti-adhesion cover over at least a portion of the area, wherein the anti-adhesion cover has a main portion, at least one opening positioned such that at least one of the first and second anchors and at least one of the third and fourth anchors are not covered by the main portion, and a flap sized to substantially cover the at least one opening in the main portion;

connecting the at least one uncovered first or second anchor and the at least one uncovered third and fourth anchor with a fourth elongate element, wherein the fourth elongate element holds at least a portion of the anti-adhesion cover within the area; and folding the flap over the at least one opening in the main portion to cover the fourth elongate element, the at least one uncovered first or second anchor, and the at least one uncovered third and fourth anchor.

* * * * *